(12) United States Patent
Dranitzki Elhalel

(10) Patent No.: US 10,000,549 B2
(45) Date of Patent: Jun. 19, 2018

(54) COMPOSITIONS AND METHODS FOR TREATMENT OF HEMATOLOGICAL MALIGNANCIES

(71) Applicants: KAHR MEDICAL LTD, Caesarea (IL); Hadasit Medical Research Services and Development Ltd., Jerusalem (IL)

(72) Inventor: Michal Dranitzki Elhalel, Shoresh (IL)

(73) Assignees: KAHR Medical Ltd., Jerusalem (IL); Hadasit Medical Research Services and Development Ltd., Jerusalem (IL)

( * ) Notice: Subject to any disclaimer, the term of this patent is extended or adjusted under 35 U.S.C. 154(b) by 0 days. days.

(21) Appl. No.: 15/178,085

(22) Filed: Jun. 9, 2016

(65) Prior Publication Data

US 2016/0340409 A1 Nov. 24, 2016

Related U.S. Application Data

(63) Continuation of application No. 13/824,423, filed as application No. PCT/IB2011/054260 on Sep. 28, 2011, now Pat. No. 9,388,230.

(60) Provisional application No. 61/387,073, filed on Sep. 28, 2010.

(51) Int. Cl.
*C07K 16/28* (2006.01)
*C07K 14/705* (2006.01)
*A61K 38/17* (2006.01)

(52) U.S. Cl.
CPC .... *C07K 14/70575* (2013.01); *A61K 38/1774* (2013.01); *C07K 14/70521* (2013.01); *C07K 14/70578* (2013.01); *C07K 2319/00* (2013.01); *C07K 2319/21* (2013.01); *C07K 2319/33* (2013.01)

(58) Field of Classification Search
CPC ............................................... C07K 14/70578
See application file for complete search history.

(56) References Cited

U.S. PATENT DOCUMENTS

| | | | |
|---|---|---|---|
| 4,892,538 A | 1/1990 | Aebischer et al. |
| 5,242,687 A | 9/1993 | Tikocinski et al. |
| 5,283,187 A | 2/1994 | Aebischer et al. |
| 5,359,046 A | 10/1994 | Capon et al. |
| 5,434,131 A | 7/1995 | Linsley et al. |
| 5,601,828 A | 2/1997 | Tikocinski et al. |
| 5,623,056 A | 4/1997 | Tykocinski et al. |
| 5,686,281 A | 11/1997 | Roberts |
| 5,770,197 A | 6/1998 | Linsley et al. |
| 5,773,253 A | 6/1998 | Linsley et al. |
| 5,821,332 A | 10/1998 | Godfrey et al. |
| 5,830,469 A | 11/1998 | Lynch et al. |
| 5,844,095 A | 12/1998 | Linsley et al. |
| 5,851,795 A | 12/1998 | Linsley et al. |
| 5,858,990 A | 1/1999 | Walsh |
| 5,885,579 A | 3/1999 | Linsley et al. |
| 5,885,776 A | 3/1999 | Stone et al. |
| 5,885,796 A | 3/1999 | Linsley et al. |
| 5,916,560 A | 6/1999 | Larsen et al. |
| 5,945,513 A | 8/1999 | Aruffo et al. |
| 5,968,510 A | 10/1999 | Linsley et al. |
| 5,977,318 A | 11/1999 | Linsley et al. |
| 5,993,800 A | 11/1999 | Linsley et al. |
| 6,046,310 A | 4/2000 | Queen et al. |
| 6,090,914 A | 7/2000 | Linsley et al. |
| 6,284,236 B1 | 9/2001 | Wiley et al. |
| 6,451,759 B1 | 9/2002 | Kang et al. |
| 6,544,523 B1 | 4/2003 | Chu |
| 6,632,789 B1 | 10/2003 | June |
| 6,727,225 B2 | 4/2004 | Wiley |
| 6,740,739 B1 | 5/2004 | Ashkenazi et al. |
| 6,746,668 B2 | 6/2004 | Ashkenazi |
| 6,824,773 B2 | 11/2004 | Wiley |
| 6,887,471 B1 | 5/2005 | Linsley et al. |
| 7,094,874 B2 | 4/2006 | Peach et al. |
| 7,041,634 B2 | 5/2006 | Weber et al. |
| 7,105,166 B1 | 9/2006 | Linsley et al. |
| 7,148,061 B2 | 12/2006 | Lenardo et al. |
| 7,208,151 B2 | 4/2007 | Browning et al. |
| 7,285,522 B2 | 10/2007 | Van Buskirk |
| 7,378,089 B2 | 5/2008 | Fathman |
| 7,482,430 B2 | 1/2009 | Wiley |
| 7,507,807 B2 | 3/2009 | Wiley |
| 7,777,004 B2 | 8/2010 | Wagner et al. |
| 9,388,230 B2 | 7/2016 | Dranitzki Elhalel |
| 2001/0026932 A1 | 10/2001 | Thomas et al. |
| 2002/0086012 A1 | 7/2002 | Wels et al. |

(Continued)

FOREIGN PATENT DOCUMENTS

EP 1016721 7/2000
EP 1634892 3/2006

(Continued)

OTHER PUBLICATIONS

Dranitzki-Elhalel et al. 2007; CD40-FasL inhibits human T cells: evidence for an auto-inhibitory loop-back mechanism. International Immunology. 19(4): 355-363.*
Carbone et al. 1995; CD40 ligand is constitutively expressed in a subset of T cell lymphomas and on the microenvironmental reactive T cells of follicular lymphomas and Hodgkin's disease. American Journal of Pathology. 147(4): 912-922.*
Tai et al. 2003; CD40 induces human multiple myeloma cell migration via phosphatidylinositol 3-kinase/AKT/NF-kB signaling. Blood . 101(7): 2762-2769.*
Tournilhac et al. 2004; Constitutive expression of CD40L on bone marrow mast cells supports the growth of lymphoplasmacytic cells in patients with Waldenstrom's macroglobulenemia. Blood. 104(11): 2350.*

(Continued)

*Primary Examiner* — Karen Cochrane Carlson

(57) ABSTRACT

Use of a chimeric protein selected from the group consisting of CTLA4-FasL and CD40-FasL proteins for treatment of lymphoma and/or a multiple myeloma and/or a leukemia as described herein, and pharmaceutical compositions and methods of treatment thereof.

22 Claims, 23 Drawing Sheets

(56) References Cited

U.S. PATENT DOCUMENTS

| | | |
|---|---|---|
| 2003/0035816 A1 | 2/2003 | Peach et al. |
| 2003/0216546 A1 | 11/2003 | Tikocinski et al. |
| 2003/0219863 A1 | 11/2003 | Peach et al. |
| 2004/0018170 A1 | 1/2004 | Shirwan |
| 2004/0038339 A1 | 2/2004 | Kufer et al. |
| 2005/0143297 A1 | 6/2005 | Rosat |
| 2005/0214311 A1 | 9/2005 | Screaton et al. |
| 2006/0280755 A1 | 12/2006 | Baron et al. |
| 2008/0260727 A1 | 10/2008 | Lanier et al. |
| 2009/0202501 A1 | 8/2009 | Zhang et al. |
| 2014/0147462 A1 | 5/2014 | Dranitzki Elhalel |

FOREIGN PATENT DOCUMENTS

| | | |
|---|---|---|
| EP | 1642907 | 4/2006 |
| EP | 1734122 | 12/2006 |
| WO | WO 03/25673 | 12/1993 |
| WO | WO 95/32627 | 12/1995 |
| WO | WO 96/07321 | 3/1996 |
| WO | WO 97/18307 | 5/1997 |
| WO | WO 99/07408 | 2/1999 |
| WO | WO 00/63253 | 10/2000 |
| WO | WO 01/45730 | 6/2001 |
| WO | WO 01/49318 | 7/2001 |
| WO | WO 03/086311 | 10/2003 |
| WO | WO 2005/016962 | 2/2005 |
| WO | WO 2005/019258 | 3/2005 |
| WO | WO 2005/051988 | 6/2005 |
| WO | WO 2005/105840 | 11/2005 |
| WO | WO 2006/009731 | 1/2006 |
| WO | WO 2007/014744 | 2/2007 |
| WO | WO 2010/005519 | 1/2010 |
| WO | WO 2011/017728 | 2/2011 |
| WO | WO 2012/042480 | 4/2012 |
| WO | WO 2004/039841 | 4/2017 |

OTHER PUBLICATIONS

Official Action dated Feb. 9, 2015 From the US Patent and Trademark Office Re. U.S. Appl. No. 13/824,423. (9 Pages).
Official Action dated Sep. 18, 2014 From the US Patent and Trademark Office Re. U.S. Appl. No. 13/824,423. (15 Pages).
Official Action dated Jul. 21, 2015 From the US Patent and Trademark Office Re. U.S. Appl. No. 13/824,423. (33 Pages).
Communication Pursuant to Article 94(3) EPC dated Apr. 3, 2014 From the European Patent Office Re. Application No. 11785094.1. (5 Pages).
Communication Pursuant to Article 94(3) EPC dated Dec. 22, 2014 From the European Patent Office Re. Application No. 11785094.1. (9 Pages).
Decision of Reexamination Dated Jan. 20, 2016 From the State Intellectual Property Office of the People's Republic of China Re. Application No. 201180046070.5. (1 Page).
International Preliminary Report on Patentability dated Apr. 2, 2013 From the International Bureau of WIPO Re. Application No. PCT/IB2011/054260. (7 Pages).
International Search Report and the Written Opinion dated Feb. 22, 2012 From the International Searching Authority Re. Application No. PCT/IB2011/054260. (10 Pages).
Notification of Office Action and Search Report dated Dec. 2, 2014 From the State Intellectual Property Office of the People's Republic of China Re. Application No. 201180046070.5 and Its Summary Into English. (8 Pages).
Notification of Office Action and Search Report dated Sep. 30, 2017 From the State Intellectual Property Office of the People's Republic of China Re. Application No. 201180046070.5 and Its Summary Into English. (9 Pages).
Notification of Office Action dated Dec. 14, 2016 From the State Intellectual Property Office of the People's Republic of China Re. Application No. 201180046070.5 and Its Summary Into English. (4 Pages).
Notification of Office Action dated Mar. 20, 2017 From the State Intellectual Property Office of the People's Republic of China Re. Application No. 201180046070.5. (4 Pages).
Notification of Office Action dated Aug. 26, 2015 From the State Intellectual Property Office of the People's Republic of China Re. Application No. 201180046070.5 and Its Summary Into English. (5 Pages).
Office Action dated Sep. 20, 2016 From the Israel Patent Office Re. Application No. 225488. (2 Pages).
Office Action dated Aug. 22, 2017 From the Israel Patent Office Re. Application No. 225488. (2 Pages).
Office Action dated Jun. 24, 2015 From the Israel Patent Office Re. Application No. 225488. (3 Pages).
Patent Examination Report dated Sep. 12, 2014 From the Australian Government, IP Australia Re. Application No. 2011309689. (3 Pages).
Patent Examination Report dated Jun. 20, 2014 From the Australian Government, IP Australia Re. Application No. 2011309689. (4 Pages).
Requisition by the Examiner dated Jun. 27, 2017 From the Canadian Intellectual Property Office Re. Application No. 2,812,057. (4 Pages).
Aktas et al. "Death Ligands and Autoimmune Demyelination", The Neuroscientist, 12(4): 305-316, Aug. 1, 2006.
Aktas et al. "Neuronal Damage in Autoimmune Neuroinflammation Mediated by the Death Ligand TRAIL", Neuron, 46(3): 421-435, May 5, 2005.
Ando et al. "TWEAK/Fn TWEAK/Fn14 Interaction Regulates RANTES Production, BMP-2-Induced Differentiation, and RANKL Expression in Mouse Osteoblastic MC3T3-E1 Cells", Arthritis Research & Therapy, 8(5): R146, Sep. 1, 2006.
Anel et al. "Apo2L/TRAIL and Immune Regulation", Frontiers in Bioscience, 12(1): 2074-2084, Jan. 1, 2007.
Ashkenazi et al. "Safety and Antitumor Activity of Recombinant Soluble Apo2 Ligand", The Journal of Clinical Investigation, 104(2): 155-162, Mar. 26, 1999.
Assohou-Luty et al. "A CD40-CD95L Fusion Protein Interferes With CD40L-Induced Prosurvival Signaling and Allows Membrane CD40L-Restricted Activation of CD95", Journal of Molecular Medicine, XP019401165, 84(9): 785-797, Published Online Aug. 4, 2006. col. 1, Line 41—col. 2, Line 14.
Baxter "The Origin and Application of Experimental Autoimmune Encephalomyelitis", Nature Reviews Immunology, 7(11): 904-912, Nov. 1, 2007.
Bevarrt et al. "Evaluation of Therapeutic Targets in Animal Models of Arthritis", Arthritis & Rheumatism, 62(8): 2192-2205, Apr. 9, 2010.
Billiau et al. "Collagen-Induced Arthritis and Related Animal Models: How Much of Their Pathogenesis is Auto-Immune, How Much is Auto-Inflammatory?", Cytokine & Growth Factor Reviews, 22(5): 399-344, Oct. 2011.
Blazar et al. "Infusion of Anti-87.1 (CD80) and Anti-87.2 (CD86) Monoclonal Antibodies Inhibits Murine Graft-Versus-Host Disease Lethality in Part Via Direct Effects on CD4+ and CD8+ T Cells", The Journal of Immunology, 157(8): 3250-3259, Oct. 15, 1996.
Bover et al. "A Previously Unrecognized Protein-Protein Interaction Between TWEAK and CD163: Potential Biological Implications", The Journal of Immunology, 178(12): 8183-8194, Jun. 15, 2007.
Brunschwig et al. "Glycosylphosphatidylinositoi-Modified Murine 87-1 and 87-2 Retain Costimulator Function", The Journal of Immunology, 155(12): 5498-5505, Dec. 15, 1995.
Burkly et al. "TWEAKing Tissue Remodeling by a Multifunctional Cytokine: Role of TWEAK/Fn14 Pathway in Health and Disease", Cytokine, 40(1): 1-16, Oct. 2007.
Campbell et al "Proinflammatory Effects of Tweak/Fn14 Interactions in Glomerular Mesangial Cells", The Journal of Immunology, 176(3): 1889-1898, Feb. 1, 2006.
Cantarella et al. "TRAIL Inhibits Angiogenesis Stimulated by VEGF Expression in Human Glioblastoma Cells", British Journal of Cancer, 94(10): 1428-1435, Apr. 11, 2006.
Chicheportiche et al. "Proinflammatory Activity of TWEAK on Human Dermal Fibroblasts and Synoviocytes: Blocking and

(56) References Cited

OTHER PUBLICATIONS

Enhancing Effects of Anti-TWEAK Monoclonal Antibodies", Arthritis Research, 4(2): 126-133, Nov. 9, 2001.
Christopherson et al. "Endothelial Induction of the T-Cell Chemokine CCL21 in T-Cell Autoimmune Diseases", Blood, 101(3): 801-806, Feb. 1, 2003.
Constantinescu et al. "Experimental Autoimmune Encephalomyelitis (EAE) as a Model for Multiple Sclerosis (MS)", British Journal of Pharmacology, 164(4): 1079-1106, Sep. 26, 2011.
Cretney et al. "TNF-Related Apoptosis-Inducing Ligand (TRAIL)/Apo2L Suppresses Experimental Autoimmune Encephalomyelitis in Mice", Immunology and Cell Biology, 83(5): 511-519, Oct. 1, 2005.
Cretney et al. "TNF-Related Apoptosis-Inducing Ligand as a Therapeutic Agent in Autoimmunity and Cancer", Immunology and Cell Biology, 84(1): 87-98, Feb. 1, 2006.
Desplat-Jego et al. "Anti-TWEAK Monoclonal Antibodies Reduce Immune Cell Infiltration in the Central Nervous System and Severity of Experimental Autoimmune Encephalomyelitis", Clinical Immunology, 117(1): 15-23, Jul. 18, 2005.
Desplat-Jego et al. "TWEAK is Expressed by Glial Cells, Induces Astrocyte Proliferation and Increases EAE Severity", Journal of Neuroimmunology, 133(1): 116-123, Dec. 2002.
Dionne et al. "CK2 Inhibition Sensitizes Chemopreventive-Induced Apoptosis of Colon Carcinoma Cells", Gastroenterology, 4(134): A-388, 2008.
Dranitzki-Elhalel et al. "CTLA-4 FasL Inhibits Allogeneic Responses In Vivo", Cellular Immunology, 239(2006): 129-135, Jul. 7, 2006.
Drexler et al. "Continuous Hematopoietic Cell Lines as Model Systems for Leukemia-Lymphoma Research", Leukemia Research, 24(2000): 881-911, May 16, 2000.
Elhalel et al. "CTLA-4 FasL Induces Alloantigen-Specific Hyporesponsiveness" The Journal of Immunology, 170(12): 5842-5850, Jun. 15, 2003.
Ellwardt et al. "Molecular Mechanisms Linking Neuroinflammation and Neurodegeneration in MS", Experimental Neurology, 262: 1-10, Dec. 1, 2014.
Eudenin et al. "Chemokine-Dependant Mechanisms of Leukocyte Trafficking Across a Model of the Blood-Brain Barrier", Methods, 29(4): 351-361, Apr. 1, 2003.
Fabregat et al. "Dysregulation of Apoptosis in Hepatocellular Carcinoma Cells", World Journal of Gastroenterology, 15(5): 513-520, Feb. 7, 2009.
Felli et al. "Multiple Members of the TNF Superfamily Contribute to IFN-Gamma-Mediated Inhibition of Erythropoiesis", The Journal of Immunology, 175(3): 1464-1472, Aug. 1, 2005.
Feng et al. "CTLA4-Fas Ligand Gene Transfer Mediated by Adenovirus Induce Long-Time Survival of Murine Cardiac Allografts", Transplantation Proceedings, 37(5): 2379-2381, Jun. 2005.
Gainer et al. "Prolongation of Allograft Survival of Transfected Islets Expressing Human CTLA4-Ig, Human Soluble Fas Ligand or a Combination of the Two", Transplantation Proceedings, 30(2): 534, Jun. 1998.
Gessner et al. "The 1gG Fc Receptor Family", Annals of Hematology, 76(6): 231-248, Jun. 1998.
Gibson et al. "Epidermal Growth Factor Protects Epithelial Cells Against Fas-Induced Apoptosis", The Journal of Biological Chemistry, 274(25): 17612-17618, Jun. 18, 1999.
Gill et al. "Insulin and Glucagon Binding to Hepatocytes in Relation to Circulating Hormones and Metabolites in Goats Maintained on Different Diets", Hormone and Metabolic Research, 13(11): 603-609, Nov. 1, 1981.
Gold et al. "Understanding Pathogenesis and Therapy of Multiple Sclerosis Via Animal Models: 70 Years of Merits and Culprits in Experimental Autoimmune Encephalomyelitis Research", Brain, 129(8): 1953-1971, Apr. 21, 2006.
Greenwald et al. "The B7 Family Revisited", Annual Review of Immunology, 23: 515-548, Jan. 19, 2005.

Griffith et al. "Monocyte-Mediated Tumoricidal Activity Via the Tumor Necrosis Factor-Related Cytokine, TRAIL", Journal of Experimental Medicine, 189(8): 1343-1354, Apr. 19, 1999.
Harada et al. "Pro-Inflammatory Effect of TWEAK/Fn14 Interaction on Human Umbilical Vein Endothelial Cells", Biochemical and Biophysical Research Communications, 299(3): 488-493, Dec. 1, 2002.
Hayakawa et al. "NK Cell TRAIL Eliminates Immature Dendritic Cells In Vivo and Limits Dendritic Cell Vaccination Efficacy", The Journal of Immunology, 172(1): 123-129, Jan. 1, 2004.
Hemmer et al. "Immunopathogenesis and Immunotherapy of Multiple Sclerosis", Nature Clinical Practice Neurology, 2(4): 201-211, Apr. 1, 2006.
Henningsson et al. "Disease-Dependent Local IL-10 Production Ameliorates Collagen Induced Arthritis in Mice", PLOS One, 7(11): e49731, Published Online Nov. 16, 2012.
Hilliard et al. "Experimental Autoimmune Encephalomyelitis in NF-kappa B-Deficient Mice: Roles of NF-kappa B in the Activation and Differentiation of Autoreactive T Cells", The Journal of Immunology, 163(5): 2937-2943, Sep. 1, 1999.
Hilliard et al. "Roles of TNF-Related Apoptosis-Inducing Ligand in Experimental Autoimmune Encephalomyelitis", The Journal of Immunology, 166(2): 1314-1319, Jan. 15, 2001.
Hirata et al. "Involvement of Regulatory T Cells in the Experimental Autoimmune Encephalomyelitis-Preventive Effect of Dendritic Cells Expressing Myelin Oligodendrocyte Glycoprotein plus TRAIL", The Journal of Immunology, 178(2): 918-925, Jan. 15, 2015.
Hirata et al. "Prevention of Experimental Autoimmune Encephalomyelitis by Transfer of Embryonic Stem Cell-Derived Dendritic Cells Expressing Myelin Oligodendrocyte Glycoprotein Peptide Along With TRAIL or Programmed Death-1 Ligand", The Journal of Immunology, 174(4): 1888-1897, Feb. 15, 2005.
Hofmann et al. "Increased Expression of ICAM-1, VCAM-1, MCP-1, and MIP-1 Alpha by Spinal Perivascular Macrophages During Experimental Allergic Encephalomyelitis in Rats", BMC Immunology, 3(1): 11, Aug. 26, 2002.
Hofstetter et al. "Therapeutic Efficacy of IL-17 Neutralization in Murine Experimental Autoimmune Encephalomyelitis", Cellular Immunology, 237(2): 123-130, Oct. 1, 2005.
Hollenbaugh et al. "Cleavable CD40Ig Fusion Proteins and the Binding to Sgp39", Journal of Immunological Methods, 188(1): 1-7, Dec. 15, 1995.
Holler et al. "Two Adjacent Trimeric Fas Ligands Are Required for Fas Signaling and Formation of a Death-Inducing Signaling Complex", Molecular and Cellular Biology, 23(4): 1428-1440, Feb. 1, 2003.
Honda et al. "Cdc42 and Rac Small G Proteins Activated by Trans-Interactions of Nectins are Involved in Activation of C-Jun N-Terminal Kinase, But Not in Association of Nectins and Cadherin to Form Adherens Junctions, in Fibroblasts", Genes to Cells, 8(5): 481-491, Apr. 10, 2003.
Huang et al. "CTLA-4-Fas Ligand Functions as A Trans Signal Converter Protein in Bridging Antigenpresenting Cells and T Cells", International Immunology, 13(4): 529-539, Apr. 1, 2001.
Hymowitz et al. "Structures of APRIL-Receptor Complexes", Journal of Biological Chemistry, 280(8): 7218-7227, Feb. 25, 2005.
Hymowitz et al. "Triggering Cell Death: The Crystal Structure of Apo2L/TRAIL in a Complex with Death Receptor 5", Molecular Cell, 4(4): 563-571, Oct. 1, 1999.
Inglis et al. "Collagen-Induced Arthritis in C57BL/6 Mice is Associated With a Robust and Sustained T-Cell Response to Type II Collagen", Arthritis Research & Therapy, 9(5): R113, Published Online Oct. 29, 2007.
Isaacs et al. "Therapy with Monoclonal Antibodies. II. The Contribution of Fc Gamma Receptor Binding and the Influence of C(H)1 and C(H)3 Domains on In Vivo Effector Function", The Journal of Immunology, 161(8): 3862-3869, Oct. 15, 1998.
Jakubowski et al. "Dual Role for TWEAK in Angiogenic Regulation", Journal of Cell Science, 115(2): 267-274, Jan. 15, 2002.
Jakubowski et al. "TWEAK Induces Liver Progenitor Cell Proliferation", Journal of Clinical Investigation, 115(9), 2330-2340, Sep. 1, 2005.

(56) References Cited

OTHER PUBLICATIONS

Janssen et al. "CD4+ T-Cell Help Controls CDS+ T -Cell Memory Via TRAIL-Mediated Activation-Induced Cell Death", Nature, 434(7029): 88-93, Published Online Mar. 3, 2005.
Jin et al. "Adenovirus-Mediated CTLA4-FasL Gene Transfer Induces Long-Term Survival of Cardiac Allograft in Rats", Zhonghua Yi Xue Za Zhi, 83(22), 1968-1974, Nov. 25, 2003, Abstract.
Jin et al. "Simultaneous Stimulation of Fas-Mediated Apoptosis and Blockade of Costimulation Prevent Autoimmune Diabetes in Mice Induced by Multiple Low-Dose Streptozotocin", Gene Therapy, 11(12): 982-911, Published Online Mar. 25, 2004.
Johnstone et al. "The TRAIL Apoptotic Pathway in Cancer Onset, Progression and Therapy", Nature Reviews Cancer, 8(10): 782-798, Published Online Oct. 1, 2008.
Jost et al. "Keratinocyte Apoptosis Induced by Ultraviolet B Radiation and CD95 Ligation ± Differential Protection Through Epidermal Growth Factor Receptor Activation and Bcl-x L Expression", Journal of Investigative Dermatology, 116(6): 860-866, Jun. 2001.
Kamata et al. "Involvement of TNF-Like Weak Inducer of Apoptosis in the Pathogenesis of Collagen-Induced Arthritis", The Journal of Immunology, 177(9): 6433-6439, Nov. 1, 2006.
Kaplan et al. "TRAIL (Apo2 Ligand) and TWEAK (Apo3 Ligand) Mediate CD4 + T Cell Killing of Antigen-Presenting Macrophages", The Journal of Immunology, XP-002974743, 164(16): 2897-2904, Mar. 15, 2000.
Kapoor et al. "Anti-CD20 Monoclonical Antibody Therapy in Multiple Myeloma", British Journal of Haematology, 141(2): 135-148, Apr. 2008.
Kawakita et al. "Functional Expression of TWEAK in Human Colonic Adenocarcinoma Cells", International Journal of Oncology, 26(1): 87-93, Published Online Jan. 1, 2005.
Kawakita et al. "Functional Expression of TWEAK in Human Hepatocellular Carcinoma: Possible Implication in Cell Proliferation and Tumor Angiogenesis", Biochemical and Biophysical Research Communications, 318(3): 726-733, Published Online May 6, 2004.
Kayagaki et al. "Polymorphism of Murine Fas Ligand That Affects the Biological Activity", Proceedings of the National Academy of Sciences, 94(8): 3914-3919, Apr. 15, 1997.
Kayagaki et al. "Suppression of Antibody Production by TNF-Related Apoptosis-Inducing Ligand (TRAIL)", Cellular Immunology, 219(2): 82-91, Oct. 1, 2002.
Kennedy et al. "Acute and Relapsing Experimental Autoimmune Encephalomyelitis are Regulated by Differential Expression of the CC Chemokines Macrophage Inflammatory Protein-1 alpha and Monocyte Chemotactic Protein-1", Journal of Neuroimmunology, 92(1): 98-108, Dec. 1, 1998.
Kennedy et al. "Induction of B Cell Costimulatory Function by Recombinant Murine CD40 Ligand", European Journal of Immunology, 24(1): 116-123, Jan. 1, 1994.
Kim et al. "TWEAK Can Induce Pro-Inflammatory Cytokines and Matrix Metalloproteinase-9 in Macrophages", Circulation Journal, 68(4): 396-399, Apr. 2004.
Kirk et al. "VEGF and Vascular Changes in Chronic Neuroinflammation", Journal of Autoimmunity, 21(4), 353-363, Published Online Sep. 10, 2003.
Komiyama et al. "IL-17 Plays an Important Role in the Development of Experimental Autoimmune Encephalomyelitis", The Journal of Immunology, 177(1): 566-573, Jul. 1, 2006.
Lamhamedi-Cherradi et al. "Critical Roles of Tumor Necrosis Factor-Related Apoptosis-Inducing Ligand in Type 1 Diabetes", Diabetes, 52(9): 2274-2278, Sep. 2003.
Lamhamedi-Cherradi et al. "Defective Thymocyte Apoptosis and Accelerated Autoimmune Diseases in TRAIL -/- Mice", Nature Immunology, 4(3): 255-260, Published Online Feb. 10, 2003.
Liu et al. "Hydrodynamics-Based Transfection in Animals by Systemic Administration of Plasmid DNA", Gene Therapy, 6(7): 1258-1266, Jul. 2, 1999.

Lu et al. "Blocking of the B7-CD28 Pathway Increases the Capacity of FasL+ (CD95L+) Dendritic Cells to Kill Alloactivated T Cells", Dendritic Cells in Fundamental and Clinical Immunology, 275-282, 1997.
Lunemann et al. "Death Ligand TRAIL Induces No Apoptosis but Inhibits Activation of Human (Auto)antigen-Specific T Cells", The Journal of Immunology, 168(10): 4881-4888, May 15, 2002.
Mackay et al. "TNF Ligands and Receptors in Autoimmunity: an Update", Current Opinion in Immunolgy, 14(6): 783-790, Dec. 1, 2002.
Maecker et al. "TWEAK Attenuates the Transition from Innate to Adaptive Immunity", Cell, 123(5): 931-944, Dec. 2, 2005.
Mahad et al. "The Role of MCP-1 (CCL2) and CCR2 in Multiple Sclerosis and Experimental Autoimmune Encephalomyelitis (EAE)", Seminars in Immunology, 15(1): 23-32, Feb. 1, 2003.
Mahalingam et al. "TRAIL Receptor Signalling and Modulation: Are We on the Right TRAIL?", Cancer Treatment Reviews, 35(3): 280-288, May 2009.
Marti-Renom et al. "Comparative Protein Structure Modeling of Genes and Genomes", Annual Review of Biophysics and Biomolecular Structure, 29(1): 291-325, Jun. 2000.
Matysiak et al. "TRAIL Induces Death of Human Oligodendrocytes Isolated From Adult Brain", Brain, 125(11): 2469-2480, Nov. 1, 2002.
Mayo Clinical Staff "Mixed Connective Tissue Disease", Mayo Foundation for Medical Education and Research, Mayoclinic.org, 1-3, Published Online May 30, 2012.
Mi et al. "Blockade of Tumor Necrosis Factor-Related Apoptosis-Inducing Ligand Exacerbates Type 1 Diabetes in NOD Mice", Diabetes, 52(8): 1967-1975, Aug. 1, 2003.
Mitsuki et al. "Siglec-7 Mediates Nonapoptotic Cell Death Independently of Its Immunoreceptor Tyrosine-Based Inhibitory Motifs in Monocytic Cell Line U937", Glycobiology, 20(3): 395-402, Mar. 1, 2010.
Mueller et al. "Targeting Fibroblast Growth Factor-Inducible-14 Signaling Protects from Chronic Relapsing Experimental Autoimmune Encephalomyelitis", Journal of Neuroimmunology, 159(1): 55-65, Feb. 2005.
Nakayama et al. "Characterization of Murine TWEAK and Its Receptor (Fn14) by Monoclonal Antibodies", Biochemical and Biophysical Research Communications, 306(4): 819-825, Jul. 11, 2003.
Nakayama et al. "Involvement of TWEAK in Interferon Gamma-Stimulated Monocyte Cytotoxicity", Journal of Experimental Medicine, 192(9): 1373-1379, Nov. 6, 2000.
Newsom-Davis et al. "Is TRAIL the Holy Grail of Cancer Therapy?", Apoptosis, 14(4): 607-623, Published Online Feb. 5, 2009.
Nitsch et al. "Direct Impact of T Cells on Neurons Revealed by Two Photon Microscopy in Living Brain Tissue", Journal of Neuroscience, 24(10): 2458-2464, Mar. 10, 2004.
Nitsch et al. "Human Brain-Cell Death Induced by Tumour-Necrosis-Factor-Related Apoptosis-Inducing Ligand (TRAIL)", The Lancet, 356(9232): 827-828, Sep. 2, 2000.
Oflazoglu et al. "Targeting CD30/CD3OL in Oncology and Autoimmune and Inflammatory Diseases", Therapeutic Targets of the TNF Superfamily, 174-185, 2009.
Orbach et al. "CD40•FasL and CTLA-4•FasL Fusion Proteins Induce Apoptosis in Malignant Cell Lines by Dual Signaling", The American Journal of Pathology, XP009155963, 177(6): 3159-3168, Dec. 2010. Abstract.
Orbach et al. "CTLA-4 • FasL Induces Early Apoptosis of Activated T Cells by Interfering With Anti-Apoptotic Signals", The Journal of Immunology, XP002668354, 179(11): 7287-7294, Dec. 1, 2007. Abstract.
Perez-Andres et al. "Clonal Plasma Cells From Monoclonal Gammopathy of Undetermined Significance, Multiple Myeloma and Plasma Cell Leukemia Show Different Expression Profiles of Molecules Involved in the Interaction With the Immunological Bone Marrow Microenvironment", Leukemia, 2005(19): 449-445, Jan. 27, 2005.
Perper et al. "TWEAK Is a Novel Arthritogenic Mediator", The Journal of Immunology, 177(4): 2610-2620, Aug. 15, 2006.

(56) References Cited

OTHER PUBLICATIONS

Perrotti et al. "Chronic Myeloid Leukemia: Mechanism of Blastic Transformation", The Journal of Clinical Investigation, 120(7): 2254-2264, Jul. 2010.
Polavarapu et al. "Tumor Necrosis Factor-Like Weak Inducer of Apoptosis Increases the Permeability of the Neurovascular Unit through Nuclear Factor-kappa B Pathway Activation", Journal of Neuroscience, 25(44): 10094-10100, Nov. 2, 2005.
Potrovita et al. "Tumor Necrosis Factor-Like Weak Inducer of Apoptosis-Induced Neurodegeneration", Journal of Neuroscience, 24(38): 8237-8244, Sep. 22, 2004.
Prasad et al. "5-Aminoimidazole-4-Carboxamide-l-Beta-4-Ribofuranoside Attenuates Experimental Autoimmune Encephalomyelitis Via Modulation of Endothelial-Monocyte Interaction", Journal of Neuroscience Research, 84(3): 614-625, Aug. 15, 2006.
Rangachari et al. "Using EAE to Better Understand Principles of Immune Function and Autoimmune Pathology", Journal of Autoimmunity, 45: 31-39, Sep. 2013.
Razmara et al. "Fn14-TRAIL, A Chimeric Intercellular Signal Exchanger, Attenuates Experimental Autoimmune Encephalomyelitis", The American Journal of Pathology, 174(2): 460-474, Feb. 2009.
Ren et al. "Involvement of Cellular Death in TRAIL/DR5-Dependent Suppression Induced by CD4 + CD25 + Regulatory T cells", Cell Death & Differentiation, 14(12): 2076-2084, Published Online Aug. 31, 2017.
Renshaw et al. "Acceleration of Human Neutrophil Apoptosis by TRAIL", The Journal of Immunology, 170(2): 1027-1033, Jan. 15, 2003.
Robinson et al. "The Experimental Autoimmune Encephalomyelitis (EAE) Model of MS: Utility for Understanding Disease Pathophysiology and Treatment", Handbook of Clinical Neurology, 122: 173-189, Apr. 9, 2014.
Rudert et al. "Apoptosis in L929 Cells Expressing a CD40/Fas Chimeric Dissociation of Stimulatory From Inhibitory Death Signalling Functions", Biochemical and Biophysical Research Communications, 204(3): 1102-1110, Nov. 15, 1994.
Saas et al. "TWEAK Stimulation of Astrocytes and the Proinflammatory Consequences", Glia, 32(1): 102-107, Oct. 1, 2000.
Schaefer et al. "TRAIL: a multifunctional cytokine", Frontiers in Bioscience: A Journal and Virtual Library, 12: 3813-3824, May 1, 2007, Abstract.
Secchiero et al. "TRAIL Counteracts the Proadhesive Activity of Inflammatory Cytokines in Endothelial Cells by Down-Modulating CCL8 and CXCL 10 Chemokine Expression and Release", Blood, 105(9): 3413-3419, Published Online Jan. 11, 2005.
Shaughnessy et al. "Integrating Cytogenetics and Gene Expression Profiling in the Molecular Analysis of Multiple Myeloma", International Journal of Hematology, 76(2): 59-64, Mar. 2002.
Shi et al. "Prolongation of Corneal Allograft Survival by CTLA4-FasL in A Murine Model", Graefe's Archive for Clinical and Experimental Ophthalmology, XP019542074, 245(11): 1691-1697, Published Online May 31, 2007. Abstract, Discussion.
Smyth et al. "Nature's TRAIL—On a Path to Cancer Immunotherapy", Immunity, 18(1): 1-6, Jan. 2003.
Song et al. "Tumor Necrosis Factor-Related Apoptosis-Inducing Ligand (TRAIL) Is an Inhibitor of Autoimmune Inflammation and Cell Cycle Progression", Journal of Experimental Medicine, 191(7): 1095-1103, Apr. 3, 2000.
Sospedra et al. "Immunology of Multiple Sclerosis", Annual Review of Immunology, 23: 683-747, Published Online Jan. 19, 2005.
Stein et al. "Novel and Emerging Drugs for Acute Myeloid Leukemia", Current Cancer Drug Targets, 12(5): 522-530, Jun. 2012.
Steinman et al. "How to Successfully Apply Animal Studies in Experimental Allergic Encephalomyelitis to Research on Multiple Sclerosis", Annals of Neurology, 60(1): 12-21, Published Online Jun. 26, 2006.
Stromnes et al. "Active Induction of Experimental Allergic Encephalomyelitis", Nature Protocols, 1(4): 1810-1819, Published Online Nov. 16, 2006.
Swaminathan et al. "Molecular Structure, Conformational Analysis, and Structure-Activity Studies of Dendrotoxin and Its Homologues Using Molecular Mechanics and Molecular Dynamics Techniques", Journal of Medicinal Chemistry, 39(11): 2141-2155, May 24, 1996.
Tanabe et al. "Fibroblast Growth Factor-Inducible-14 Is Induced in Axotomized Neurons and Promotes Neurite Outgrowth", Journal of Neuroscience, 23(29): 9675-9686, Oct. 22, 2003.
Timmer et al. "Fas Receptor-Mediated Apoptosis: a Clinical Application?" The Journal of Pathology, 196(2): 125-132, Published Online Nov. 28, 2001.
Tournilhac et al. "Constitutive Expression of CD40L on Bone Marrow Mast Cells Supports the Growth of Lymphoplasmatic Cells in Patients with Waldenstrom's Macroglobulinemia", Blood, 104(11): 2350, 2004, Abstract.
Tykocinski et al. "New Designs for Cancer Vaccine and Artificial Veto Cells", Immunologic Research, 27(2-3): 565-574, Jun. 2003.
van Kooten et al. "CD40-CD40 Ligand", Journal of Leukocyte Biology, 67(1): 2-17, Jan. 2000.
Vince et al. "TWEAK Shall Inherit the Earth", Cell Death & Differentiation, 13(11): 1842-1844, Published Online Aug. 25, 2006.
Vitale et al. "Engagement of p75/AIRM1 or CD33 Inhibits the Proliferation of Normal or Leukemic Myeloid Cells", Proceedings of the National Academy of Sciences, 96(26): 15091-15096, Dec. 21, 1999.
Walczak et al. "Tumoricidal Activity of Tumor Necrosis Factor Related Apoptosis Inducing Ligand In Vivo", Nature Medicine, 5(2): 157-163, Feb. 1, 1999.
Wandinger et al. "TNF-Related Apoptosis Inducing Ligand (TRAIL) as a Potential Response Marker for Interferon-Beta Treatment in Multiple Sclerosis", The Lancet, 361(9374): 2036-2043, Jun. 14, 2003.
Wang et al. "A Mechanism of Cell Survival: Sequestration of Fas by the HGF Receptor Met", Molecular Cell, 9(2): 411-421, Feb. 2002.
Watts et al. "TNF/TNFR Family Members in Costimulation of T Cell Responses", Annual Review of Immunology, 23: 23-68, Apr. 23, 2005.
Weiss et al. "CD8 + T Cells in Inflammatory Demyelinating Disease", Journal of Neuroimmunology, 191(1): 79-85, Nov. 2007.
Wiley et al. "TWEAK, a Member of the TNF Superfamily, is a Multifunctional Cytokine That Binds the TweakR/Fn 14 Receptor", 14(3): 241-249, Jun. 1, 2003.
Winkles "The TWEAK-Fn 14 Cytokine-Receptor Axis: Discovery, Biology and Therapeutic Targeting", Nature Reviews Drug Discovery, 7(5): 411-425, May 1, 2008.
Wong et al. "PECAM-1/CD31 Trans-Homophilic Binding at the Intercellular Junctions Is Independent of Its Cytoplasmic Domain; Evidence for Heterophilic Interaction with Integrin alpha V beta 3 in Cis", Molecular Biology of the Cell, 11(9): 3109-3121, Sep. 2000.
Xu et al. "TWEAK/Fn14 Interaction Stimulates Human Bronchial Epithelial Cells to Produce IL-8 and GM-SF", Biochemical and Biophysical Research Communications, 318(2): 422-427, May 2004.
Yepes et al. "Inhibition of TWEAK Activity as a New Treatment for Inflammatory and Degenerative Diseases", Drug News Perspect, XP-001539589, 19(10): 589-595, Dec. 2006.
You et al. "Apoptosis of Dendritic Cells Induced by Decoy Receptor 3 (DcR3)", Blood, 111(3): 1480-1488, Feb. 1, 2008.
Zamvil et al. "The T Lymphocite in Experimental Allergic Encephalomyelitis", Annual Review of Immunology, 8(1): 579-621, Apr. 1990.
Zauli et al. "The Role of the TRAIL/TRAIL Receptors System in Hematopoiesis and Endothelial Cell Biology", Cytokine & Growth Factor Reviews, 17(4): 245-257, Aug. 2006.
Zhang et al. "Reciprocal Expression of TRAIL and CD95L in Th1 and Th2 Cells: Role of Apoptosis in T Helper Subset Differentiation", Cell Death and Differentiation, 10(2): 203-210, Feb. 2003.
Zhao et al. "TWEAK/Fn14 Interactions Are Instrumental in the Pathogenesis of Nephritis in the Chronic Graft-versus-Host Model of Systemic Lupus Erythematosus", The Journal of Immunology, 179(11): 7949-7958, Dec. 1, 2007.

\* cited by examiner

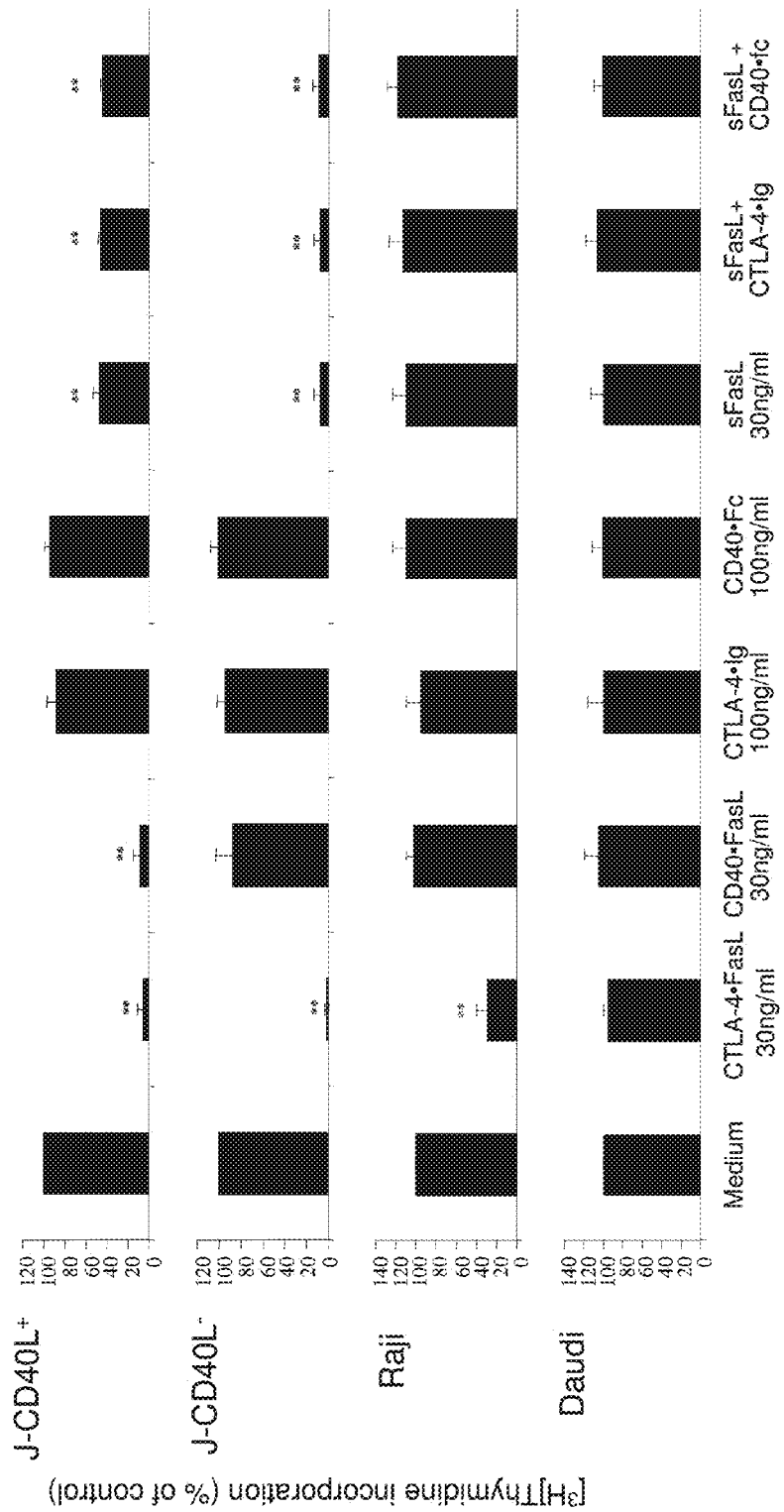

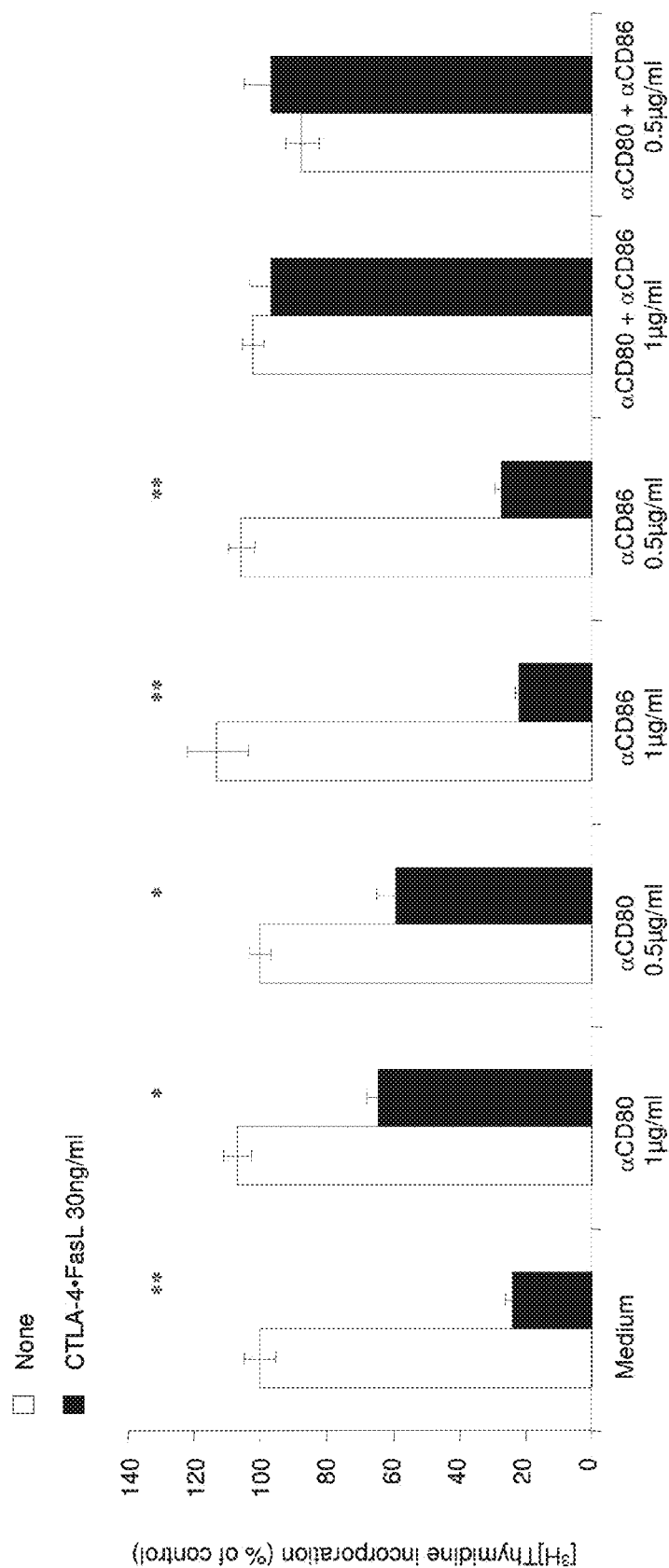

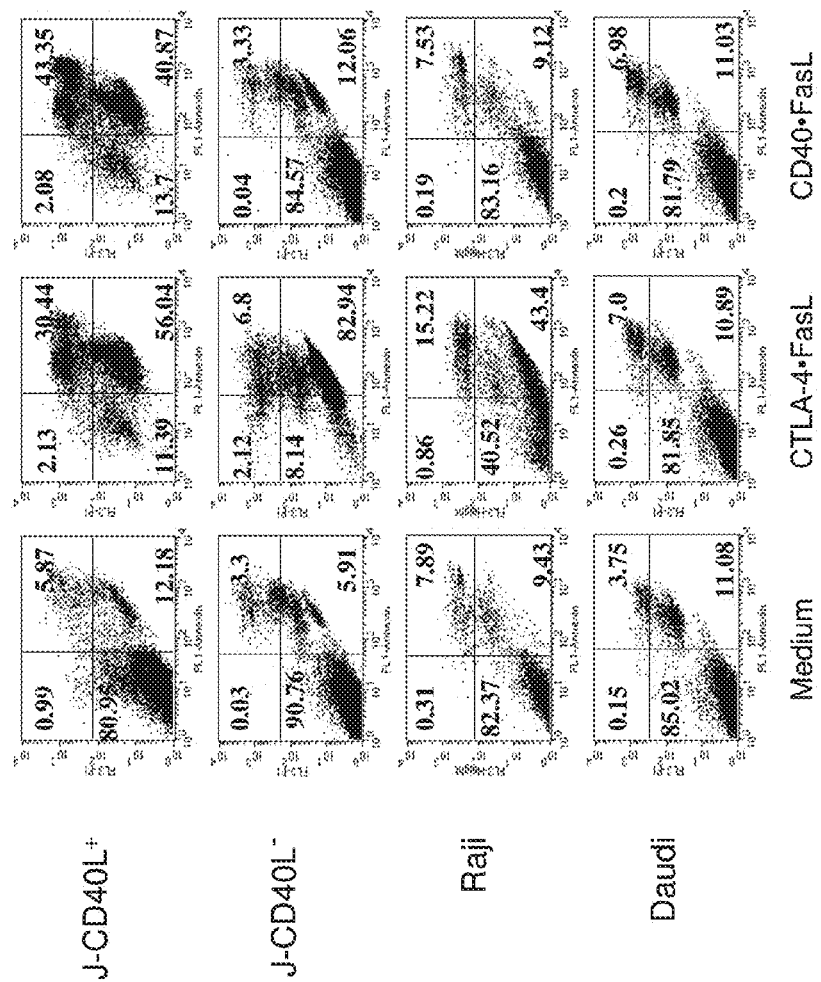

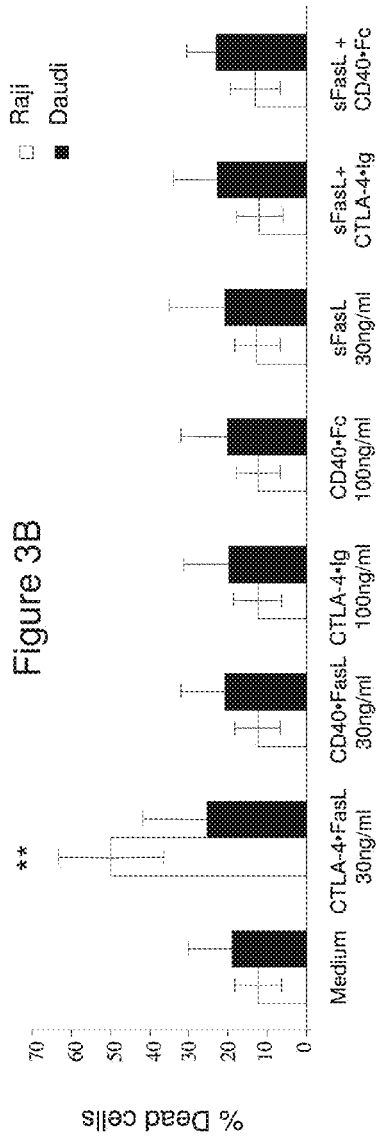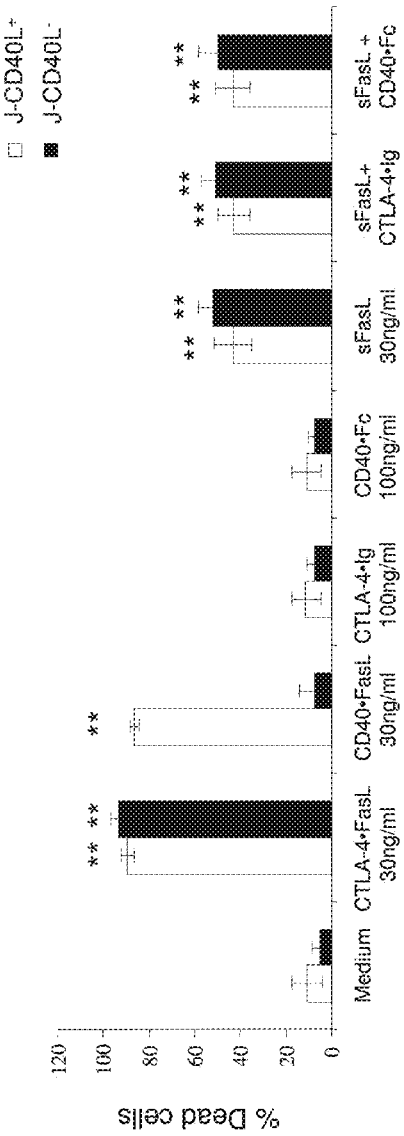

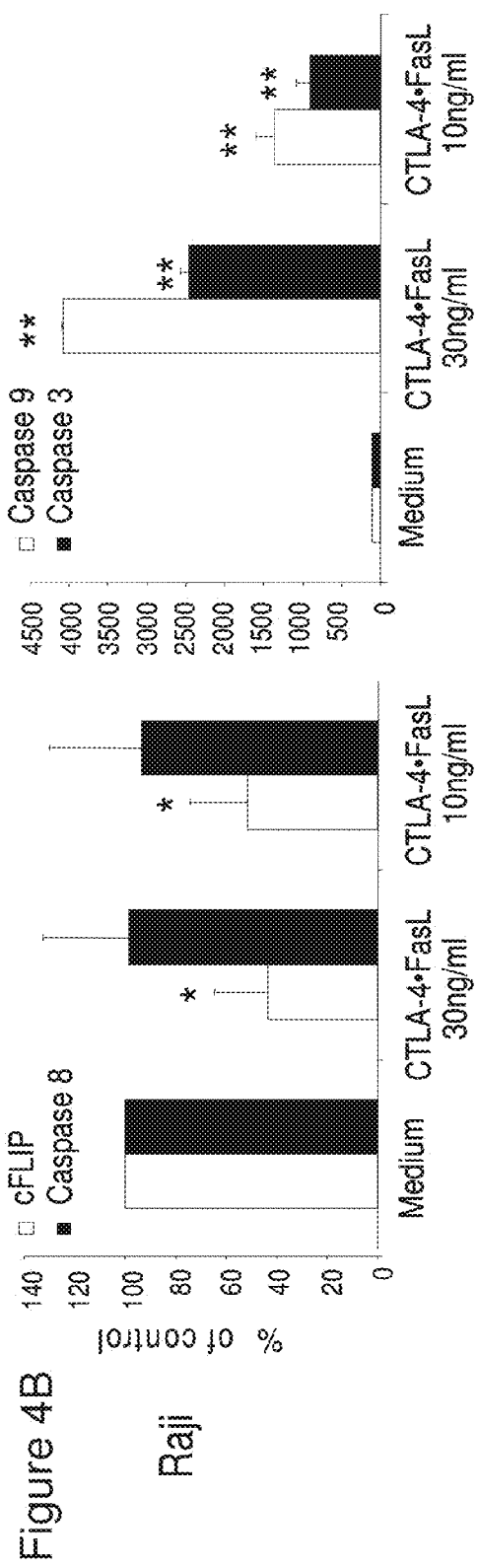
Figure 4B Raji

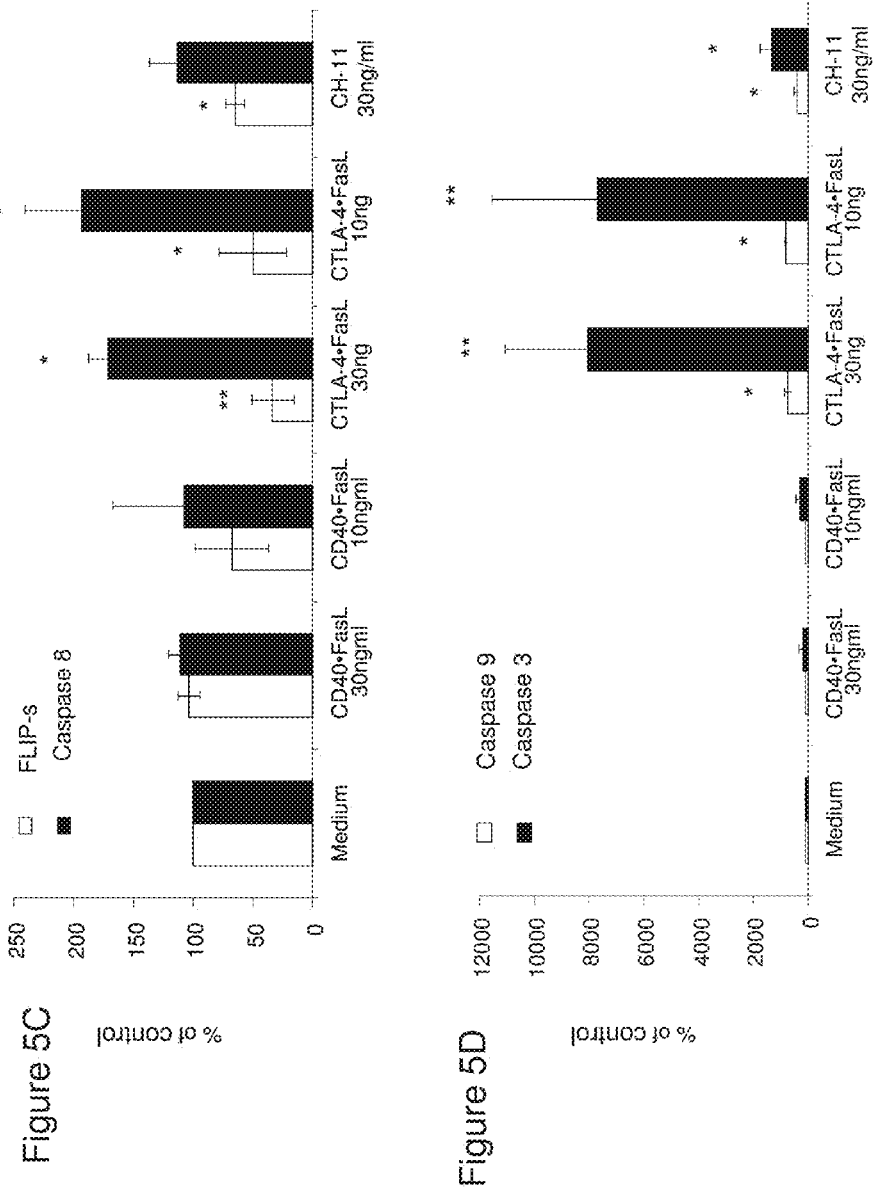

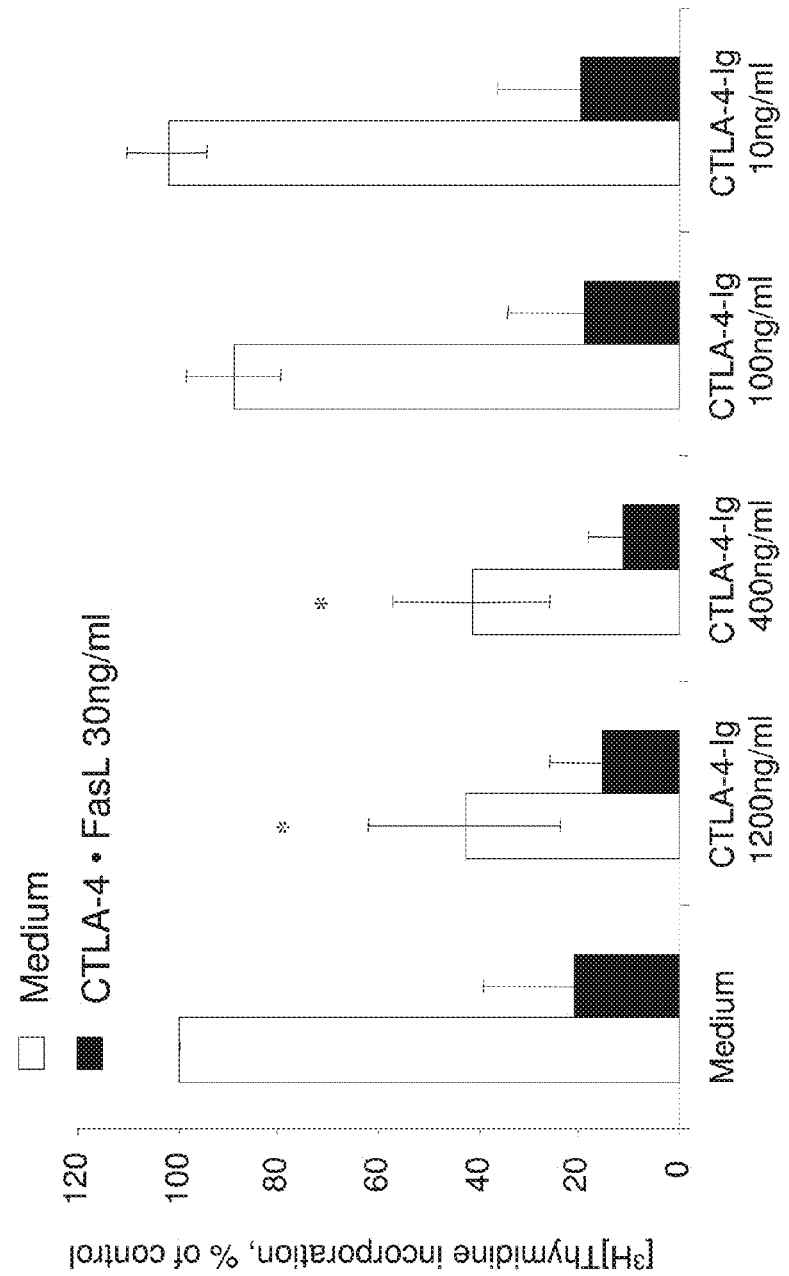

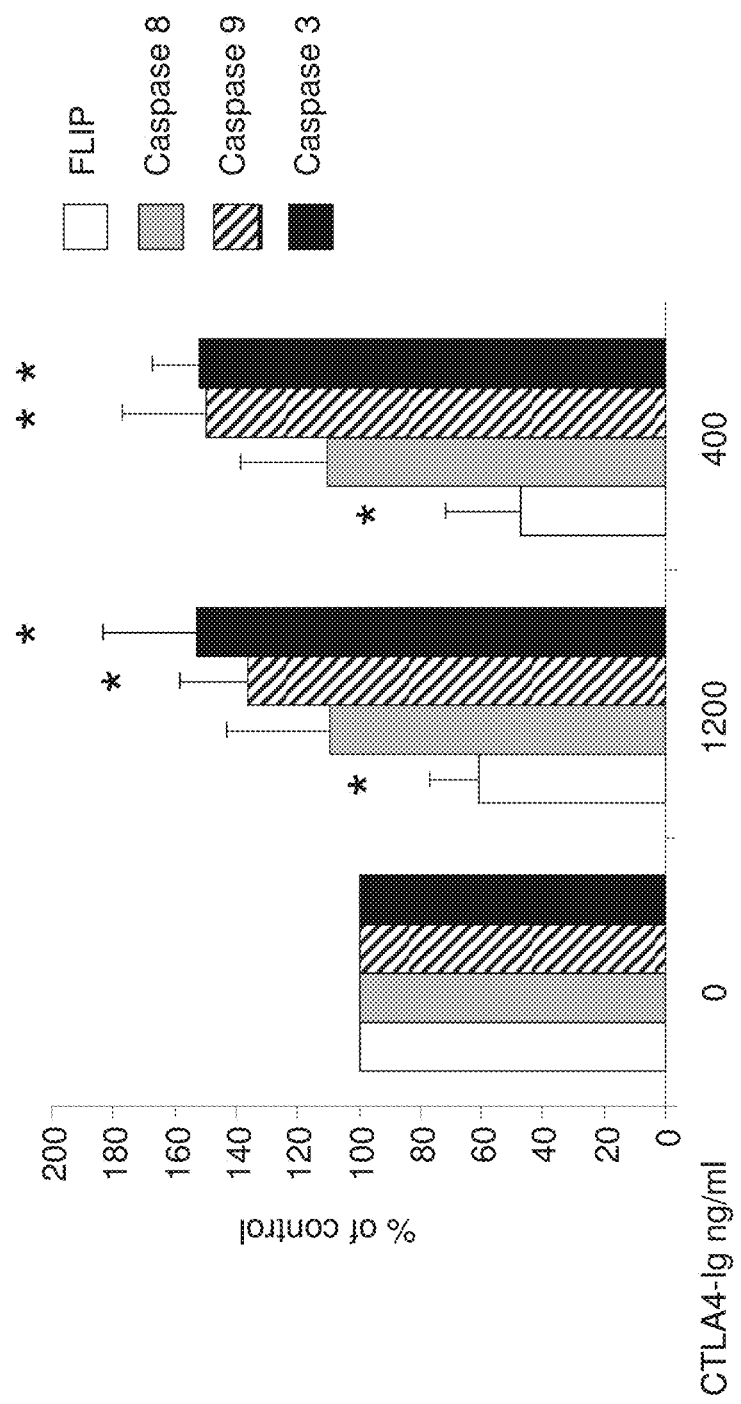

COMPOSITIONS AND METHODS FOR TREATMENT OF HEMATOLOGICAL MALIGNANCIES

CROSS-REFERENCE TO RELATED APPLICATIONS

This application is a continuation of U.S. patent application Ser. No. 13/824,423, which entered the National Stage in the United States under 35 U.S.C. § 371 on Jul. 28, 2013, from International Application No. PCT/IB2011/054260, International Filing Date Sep. 28, 2011, claiming the benefit of U.S. Provisional Patent Application No. 61/387,073, filed Sep. 28, 2010, all of which are hereby incorporated by reference.

This invention relates to compositions and methods for treatment of hematological malignancies, and in particular, but not exclusively, to fusion proteins and compositions and methods of use thereof.

BACKGROUND OF THE INVENTION

There are two major arms to the immune system, supported by different types of cells called B-lymphocytes and T-lymphocytes (B-cells and T-cells). B cells make antibodies when they encounter antigens and, in most instances, these antibodies are protective. In autoimmune diseases, however, some of the antibodies react with the individual's tissues. When they deposit in tissue, they cause an inflammatory reaction and tissue damage. T-cells, like B-cells, are also activated when they encounter an antigen. As T-cells develop they undergo a process called "thymic education." During thymic education, more than 95% of the T-cells die. The T-cells that have had a T-cell receptor that can recognize and react with the individuals's own tissues (self-antigens) are specifically eliminated. Some autoreactive T-cells escape the elimination process, however, and can initiate an immune response that results in autoimmune disease.

The modulation of T-cell activity remains a significant therapeutic goal in diseases with immunopathological T-cells. The fate of T lymphocytes following T cell receptor (TCR) stimulation is guided by the integration of costimulatory and inhibitory receptor inputs. Costimulatory ligands on antigen-presenting cells (APC) trigger cognate receptor molecules on T cells, with resultant enhancement of T cell proliferation, cytokine secretion, and differentiation. In contrast, binding of inhibitory ligand molecules to cognate counter-receptors on T lymphocytes diminishes effector functioning by inducing T cell unresponsiveness or programmed cell death (PCD) (also referred to as apoptosis). Costimulatory and inhibitory receptor pathway interactions are suggested by experiments demonstrating increased inhibitor activity in the presence of costimulator blockade.

Cytotoxic T lymphocyte-associated protein-4 (CTLA-4 (CD152)) is an inhibitory receptor molecule that is expressed on the surface of activated T lymphocytes. Following engagement with the B7-1 (CD80) and/or B7-2 (CD86) ligands resident on APC, the CTLA-4 counter-receptor, via associated SHP-2 phosphatase, inhibits T cell activation. On activated T cells, CTLA-4 exists as disulfide-linked homodimeric glycoprotein complexes. A recombinant, soluble CTLA-4:immunoglobulin G (CTLA-4:Ig) chimeric protein demonstrates inhibitory function by competitively blocking CD80/CD86 molecule binding to the activating CD28 acceptor on T cell surfaces. CTLA-4:Ig also exhibits immunosuppressive activity in animal models of graft rejection and autoimmune disease by blocking T cell costimulation through CD28. In addition, intracellular T cell survival signaling through CD28 is antagonized by APC treatment with CTLA-4:Ig, which can increase susceptibility to Fas-dependent PCD. The action of CTLA-4, as well as CTLA-4:Ig fusion proteins, are discussed in U.S. Pat. Nos. 5,885,776; 5,885,579; 5,851,795; and 5,968,510.

Apoptosis (or PCD) is a distinct form of cell death which is essential for the regulation of cellular homeostasis. In the immune system, Fas (CD95) receptor and its ligand, FasL (CD95L), participate in various processes involved in the induction of apoptosis, including immune cell-mediated cytotoxicity, and in the regulation of cellular immune responses. FasL is a member of the tumor necrosis factor superfamily and is expressed by a restricted subset of immune cells, including monocytes, NK cells, and activated B and T cells. On the cell surface, FasL is oriented as a type II membrane protein within trimeric complexes. Metalloproteinase cleavage of membrane-associated FasL releases soluble FasL (sFasL) trimers from the membrane. The FasL molecule triggers Fas-dependent PCD.

The valency of a molecule or molecular complex can be increased by association with the cell surface. Different coding sequences of recombinant sFasL molecules affect macromolecular aggregation and, in turn, affect sFasL pro-apoptotic function. In particular, a naturally processed sFasL molecule forms trimers and poorly induces apoptosis. In contrast, a recombinant full-length extracellular domain sFasL polypeptide forms higher order aggregates and displays highly potent apoptotic activity. Furthermore, complexes of sFasL produced by recombinant expression in human 293 cells require cross-linking for lysis of Fas-sensitive cells.

U.S. Pat. No. 5,830,469 discloses monoclonal antibodies and binding proteins that specifically bind to human Fas antigen; some of the antigens and antibodies are reported as stimulating T cell proliferation, inhibiting of anti-Fas CH-11 monoclonal antibody-mediated lysis of cells, and blocking Fas ligand-mediated lysis of cells. Fas-Fc fusion proteins are also disclosed.

U.S. Pat. Nos. 5,242,687; 5,601,828; and 5,623,056 disclose various fusion proteins containing a CD8 component that bind to a cell but do not mask a signal produced by the cell.

U.S. Pat. No. 5,359,046 discloses chimeric proteins comprised of an extracellular domain capable of binding to a ligand in a non-MHC restricted manner, a transmembrane domain and a cytoplasmic domain capable of activating a signaling pathway. Similar technology is disclosed in U.S. Pat. No. 5,686,281.

SUMMARY OF THE INVENTION

The background art does not teach or suggest methods of treatment of lymphoma and multiple myeloma through the administration of chimeric proteins which are useful for both blocking and signaling.

The present invention, in at least some embodiments, overcomes these drawbacks of the background art by providing methods of treatment of lymphoma and/or multiple myeloma through the administration of chimeric proteins which are useful for both blocking and signaling.

In at least some embodiments, there is provided pharmaceutical compositions containing such chimeric proteins, adapted for treatment of lymphoma and/or multiple myeloma.

By "lymphoma" it is meant a malignant growth of B or T cells in the lymphatic system, optionally including Hodgkin's lymphoma or non-Hodgkin's lymphoma (NHL).

According to at least some embodiments, the non-Hodgkin's Lymphoma is a selected from the group consisting of aggressive NHL, transformed NHL, indolent NHL, relapsed NHL, refractory NHL, low grade non-Hodgkin's Lymphoma, follicular lymphoma, large cell lymphoma, B-cell lymphoma, T-cell lymphoma, Mantle cell lymphoma, Burkitt's lymphoma. NK cell lymphoma, diffuse large B-cell lymphoma, acute lymphoblastic lymphoma, and cutaneous T cell cancer, including mycosos fungoides/Sezry syndrome.

An "indolent" non-Hodgkin's Lymphoma is a classification that includes slow growing forms of lymphoma. They encompass what are called low grade and some categories of intermediate grade NHL in the Working Formulation. Indolent NHLs are sometimes not responsive to conventional cancer therapies such as chemotherapy and radiation therapy. Indolent NHL and other premalignant forms of NHL may also proceed to NHL. With regard to premalignant or benign forms of the disease, optionally the compositions and methods thereof may be applied for prevention, in addition to or in place of treatment, for example optionally to halt the progression of the disease to a malignant form of NHL.

A "transformed" non-Hodgkin's Lymphoma is a classification sometimes employed to describe an indolent NHL which acquires an aggressive aspect and becomes more responsive to standard chemotherapies.

By "multiple myeloma" it is meant any type of B-cell malignancy characterized by the accumulation of terminally differentiated B-cells (plasma cells) in the bone marrow.

According to at least some embodiments, the multiple myeloma is selected from the group consisting of multiple myeloma cancers which produce light chains of kappa-type and/or light chains of lambda-type; and/or aggressive multiple myeloma, including primary plasma cell leukemia (PCL); and/or optionally including benign plasma cell disorders such as MGUS (monoclonal gammopathy of undetermined significance) and/or Waldenström's macroglobulinemia (WM, also known as lymphoplasmacytic lymphoma) which may proceed to multiple myeloma; and/or smoldering multiple myeloma (SMM), and/or indolent multiple myeloma, premalignant forms of multiple myeloma which may also proceed to multiple myeloma; and/or primary amyloidosis. With regard to premalignant or benign forms of the disease, optionally the compositions and methods thereof may be applied for prevention, in addition to or in place of treatment, for example optionally to halt the progression of the disease to a malignant form of multiple myeloma.

According to at least some embodiments of the present invention, there is provided a method of treatment of a leukemia selected from the group consisting of acute non-lymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

In at least some embodiments, there is provided pharmaceutical compositions containing such chimeric proteins, adapted for treatment of a leukemia selected from the above group.

According to at least some embodiments of the present invention, the chimeric protein is selected from the group consisting of CTLA4-FasL and CD40-FasL proteins.

U.S. Pat. No. 7,569,663 to Tykocinski, et al., issued on Aug. 4, 2009, which is hereby incorporated by reference as if fully set forth herein, describes chimeric proteins that function as both a blocking protein and a signaling protein. Such chimeric proteins include CTLA4-FasL and CD40-FasL proteins. Data was also provided in this patent that demonstrates the efficacy of the CTLA-4-FasL chimeric protein to inhibit the polyclonal proliferation of human peripheral blood T cells to mitogenic anti-CD3 antibody. Methods of use and of production are also described.

As used herein the term "treatment" refers to care provided to relieve illness and refers to both a therapeutic treatment or prophylactic/preventative measures, wherein the objective is to prevent or slow down (lessen) the targeted pathologic condition or disorder. Those in need of treatment include those already with the disorder as well as those prone to have the disorder or those in whom the disorder is to be prevented. The term treatment as used herein refers also to "maintenance therapy", which is a treatment that is given to keep a pathologic condition or disorder from coming back after it has disappeared following the initial therapy.

The term "therapeutically effective amount" refers to an amount of agent according to the present invention that is effective to treat a disease or disorder in a mammal.

According to any of the above described embodiments of chimeric proteins and/or pharmaceutical compositions thereof, alone or in combination with other therapeutics or drugs (for combination therapy), there is provided, according to at least some embodiments of the present invention, compositions and methods of treatment therefore for treatment of a hematological malignancy as described herein. Such one or more additional therapeutics or drugs could easily be selected by one of ordinary skill in the art.

As used herein the term "combination therapy" refers to the simultaneous or consecutive administration of two or more medications or types of therapy to treat a single disease, preferably with a synergistic effect. In particular, the term refers to the use of any of the chimeric proteins or pharmaceutical compositions according to at least some embodiments of the invention in combination with at least one additional medication or therapy. Thus, treatment of a disease using the agents according to at least some embodiments of the present invention may be combined with therapies well known in the art that include, but are not limited to, radiation therapy, antibody therapy, chemotherapy or surgery or in combination therapy with other biological agents, conventional drugs, anti-cancer agents, immunosuppressants, cytotoxic drugs for cancer, chemotherapeutic agents.

According to at least some embodiments, treatment of Multiple Myeloma using the agents according to at least some embodiments of the present invention may be combined with an agent including but not limited to Melphalan, thalidomide (MPT), or combination Bortezomib (Velcade), melphalan, prednisone (VMP) or a combination of Lenalidomide plus low-dose dexamethasone; and/or bio-phosphonates; chemotherapy (e.g., alkylating agents, vincristine, doxorubicin); autologous stem cell transplantation; and corticosteroids (e.g., prednisone and dexamethasone).

According to at least some embodiments, treatment of leukemia using the agents according to at least some embodiments of the present invention may be combined with an agent including but not limited to alpha-interferon: interleukin-2; cytarabine and mitoxantrone; cytarabine and daunorubicin and 6-thioguanine; cyclophosphamide and 2-chloro-2'-deoxyadenosine; VP-16 and cytarabine and idorubicin or mitoxantrone; fludarabine and cytarabine and .gamma.-CSF; chlorambucil; cyclophosphamide and vincristine and (prednisolone or prednisone) and optionally doxorubicin; tyrosine kinase inhibitor; and antibody; glutamine; clofibric acid; all-trans retinoic acid; ginseng diyne analog; KRN8602 (anthracycline drug); temozolomide and poly(ADP-ribose) polymerase inhibitors; lysofylline; cytosine arabinoside; chlythorax and elemental enteral diet enriched with medium-chain triglycerides; amifostine; and gilvusmycin.

According to at least some embodiments, treatment of lymphoma using the agents according to at least some embodiments of the present invention may be combined with an agent including but not limited to a vinca alkaloid, such as vincristine, vinblastine, vindesine, or vinorelbine; an anthracycline such as doxorubicin; combinations such as CHOP (vincristine, cyclophosphamide, doxorubicin and prednisone); and other suitable alkaloids including, but not limited to, the podophyllins, podophyllotoxins, and derivatives thereof (e.g., etoposide, etoposide phosphate, teniposide, etc.), the camptothecins (e.g., irinotecan, topotecan, etc.) the taxanes (taxol, etc.), and derivatives thereof.

As used herein, the term "synergistic effect" or "synergism" refers to a greater effect seen with a combination of a plurality of therapeutic agents, including at least one therapeutic agent according to any embodiment of the present invention, in which the therapeutic effect is greater than the additive effects of the plurality of agents when administered singly. By "greater therapeutic effect", it is meant a greater cancer effect and/or a reduction in one or more side effects.

As used herein, the term "subject" includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc.

BRIEF DESCRIPTION OF THE DRAWINGS

FIG. 2. Susceptibility to J-CD40L+ and J-CD40L− cells to CTLA-4•FasL and CD40•FasL is dependent on expression of the relevant counterreceptors. A. CD40L-expressing (J-CD40L+) and non-expressing (J-CD40L−) malignant T cells (upper two panels), and Raji and Daudi malignant B cells (lower two panels), were plated (0.5×105) in round-bottom, 96-well plates in the presence or absence of CTLA-4•FasL, CD40•FasL, or sFas (30 ng/ml each), or CTLA-4•Ig or CD40-Fc (100 ng/ml each, or indicated combinations. Cells were pulsed with [3H]thymidine and incubated for 18 h. Assays were performed in triplicate. Data is presented as percentage of [3H]thymidine incorporation of cells in incubated in growth medium. The results shown summarize 3 independent experiments for each cell line. *P<0.05 versus control, P<0.01 versus control. B. 0.5×105 Raji cells were incubated with (black bars) or without (white bars) CTLA-4•FasL (30 ng/ml) in the presence of either anti-CD80 or anti-CD86 Ab (B7 blockers) or their combination for 18 h. Proliferation was determined and presented as in A. These results summarize three independent experiments. p<0.05, p<0.01 vs. medium.

FIG. 3. Susceptibility of J-CD40L+ and J-CD40L− cells to apoptosis induction by CTLA-4•FasL and CD40•FasL is dependent on their expression of relevant counter-receptors. J-CD40L+, CD40L (J-CD40L−). Raji and Daudi cells were incubated in the presence or absence of either CTLA-4•FasL, CD40•FasL, or sFas (30 ng/ml each), or CTLA-4•Ig or CD40-Fc (100 ng/ml each, or indicated combinations, for 4 h (T cells) or 16 h (B cells). 26 Cells were harvested, co-stained with Annexin V and PI, and analyzed by flow cytometry. A. A representative dot plot analysis of the cell lines in the presence or in the absence of CTLA-4•FasL or CD40•FasL. B-C. Percentage of dead cells (Annexin V+/PI−+Annexin V+/PI+) obtained from FACS analysis of Jurkat malignant T cell lines (B), Raji and Daudi malignant B cell lines (C). The summary of three independent experiments is shown. Data are presented as mean±SD. **p<0.01 vs. medium.

DESCRIPTION OF EXEMPLARY EMBODIMENTS

Figure 1:
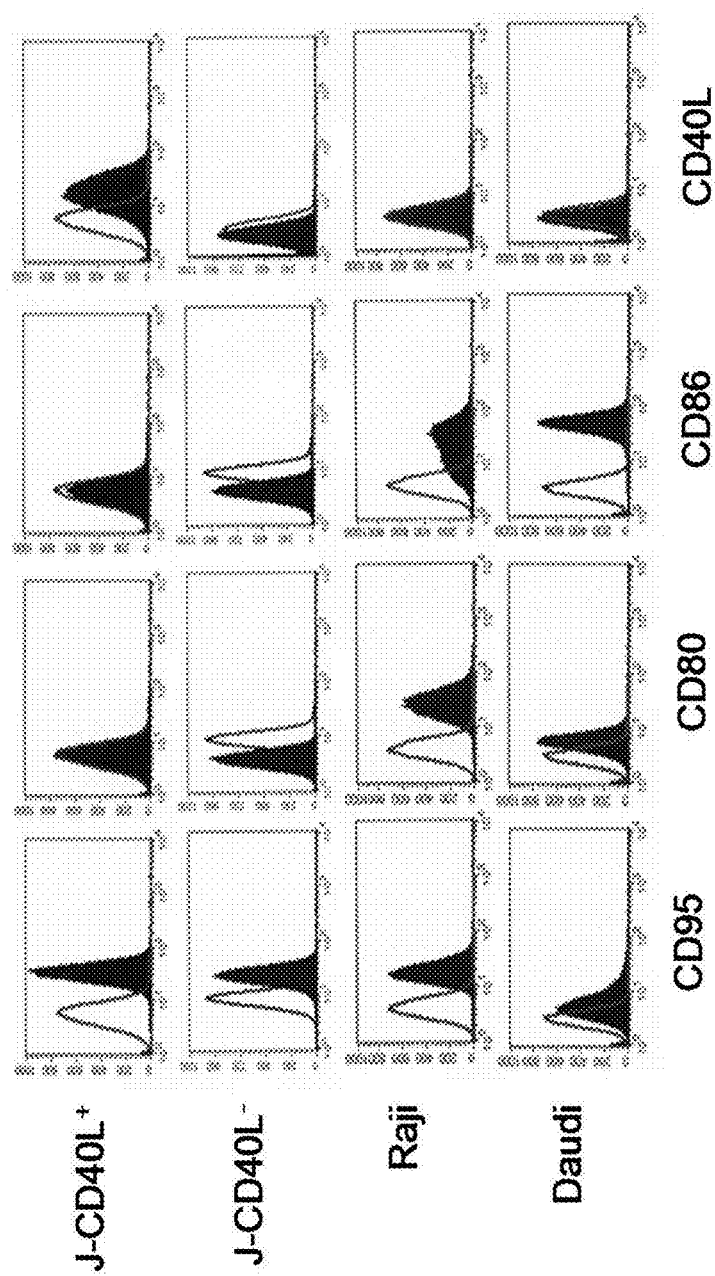
FIG. 1. Expression of fusion protein counter-receptors on T and B malignant cell lines. CD40L-expressing (J-CD40L+) and non-expressing (JCD40L−) malignant T cell lines, as well as Raji and Daudi malignant B cell lines, were immuno-stained with FITC-conjugated anti-CD95, anti-CD80, anti-CD86 or anti-CD40L mAb (in black), or with isotype control Ab (white), and then analyzed by flow cytometry, as described in Methods.

According to at least some embodiments of the present invention, there is provided methods of treatment of lymphoma and/or multiple myeloma through the administration of chimeric proteins which are useful for both blocking and signaling.

According to at least some embodiments, the chimeric protein is provided in a pharmaceutical composition, comprising the protein and a pharmaceutically suitable carrier.

A pharmaceutical composition according to at least some embodiments of the present invention can be administered via one or more routes of administration using one or more of a variety of methods known in the art. As will be appreciated by the skilled artisan, the route and/or mode of administration will vary depending upon the desired results. Preferred routes of administration for therapeutic agents of the invention include intravascular delivery (e.g. injection or infusion), intravenous, intramuscular, intradermal, intraperitoneal, subcutaneous, spinal, oral, enteral, rectal, pulmonary (e.g. inhalation), nasal, topical (including transdermal, buccal and sublingual), intravesical, intravitreal, intraperitoneal, vaginal, brain delivery (e.g. intra-cerebroventricular, intracerebral, and convection enhanced diffusion), CNS delivery (e.g. intrathecal, perispinal, and intra-spinal) or parenteral (including subcutaneous, intramuscular, intravenous and intradermal), transmucosal (e.g., sublingual administration), administration or administration via an implant, or other parenteral routes of administration, for example by injection or infusion, or other delivery routes and/or forms of administration known in the art. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the chimeric protein may be coated in a material to protect the protein from the action of acids and other natural conditions that may inactivate the protein.

A pharmaceutical composition according to at least some embodiments of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. Examples of suitable aqueous and nonaqueous carriers that may be employed in the pharmaceutical compositions according to at least some embodiments of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions according to at least some embodiments of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, optionally from about 0.1 percent to about 70 percent, optionally from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms according to at least some embodiments of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the chimeric protein, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months.

Alternatively, the chimeric protein can be administered as a sustained release formulation, in which case less frequent administration is required. Dosage and frequency vary depending on the half-life of the chimeric protein in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions according to at least some embodiments of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions according to at least some embodiments of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of a chimeric protein according to at least some embodiments of the invention preferably results in a decrease in severity of disease symptoms, an increase in frequency and duration of disease symptom-free periods, an increase in lifespan, disease remission, or a prevention of impairment or disability due to the disease affliction. For example, for the treatment of Multiple Myeloma, lymphoma and/or leukemia, a "therapeutically effective dosage" optionally inhibits cell growth or tumor growth by at least about 20%, 40%, 60%, 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. Alternatively or additionally, the suitable amount or dosage may also optionally be at least partially selected according to the administration of one or more additional treatments for multiple myeloma, which may optionally and preferably have a synergistic effect and so which may optionally cause the dosage amount to be adjusted. Such one or more additional treatments could easily be selected by one of ordinary skill in the art.

Alternatively or additionally, a "therapeutically effective dosage" preferably results in at least stable disease, preferably partial response, more preferably complete response, as assessed by the WHO or RECIST criteria for tumor response (Natl Cancer Inst 1999; 91:523-8 and Cancer 1981; 47:207-14).

A therapeutically effective amount of a therapeutic compound can decrease tumor size, or otherwise ameliorate symptoms in a subject, or otherwise support partial or complete stable disease and/or partial or complete response as determined above. One of ordinary skill in the art would be able to determine such amounts based on such factors as the subject's size, the severity of the subject's symptoms, and the particular composition or route of administration selected.

Therapeutic compositions can be administered with medical devices known in the art. For example, in a preferred embodiment, a therapeutic composition according to at least some embodiments of the invention can be administered with a needles hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the chimeric protein according to at least some embodiments of the invention can be formulated to ensure proper distribution in vivo. For example, the blood-brain barrier (BBB) excludes many highly hydrophilic compounds. To ensure that the therapeutic compounds according to at least some embodiments of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J Physiol. 1233:134); p 120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273.

The following examples are offered for illustrative purposes only, and are not intended to limit the scope of the present invention in any way.

All patent and literature references cited in the present specification are hereby incorporated by reference in their entirety.

Example 1—Efficacy of Chimeric Protein for Treatment of Hematological Malignancies Materials and Methods Cells, Abs, Reagents, and Fusion Proteins Daudi, Raji, and JY and 293 human kidney cell lines were originally obtained from the American Type Culture Collection (ATCC) (Bethesda, Md., USA). Two Jurkat sublines (J-CD40L+ and J-CD40L-) were kindly provided by Dr. John Fayen (CWRU. Cleveland, Ohio, USA). All cell lines were followed weekly to verify that they retained their original appearance and growing rates, and remained free of contamination. Also, cells were repeatedly tested to verify continued expression of expected surface molecules. If any change was suspected, new lots were thawed. Medium was tested for mycoplasma contamination using a commercial PCR kit (Biological Industries. Israel).

FITC-conjugated fluorescent Ab specific for CD40L, CD80, CD86 and CD95, along with their matched FITC-conjugated IgG isotypes, were purchased from PharMingen (San Diego, Calif., USA). Recombinant human CTLA-4•Ig (CTLA-4/Fc) and sFasL were purchased from R&D Systems (MN, USA) and Alexis Biochemicals (San Diego, Calif.), respectively. CD40-Fc fusion protein was purchased from Calbiochem (Darmstadt, Germany). Anti-human B7-1 & B7-2 (CD80 and 86) Ab were purchased from R&D Systems. For Western blot analysis, anti-β actin Ab and anti-mouse GAPDH Ab were purchased from Sigma-Aldrich and Chemicon International, respectively. Anti-FLIPS/L and anti-Caspase 8 pAb were purchased from Santa Cruz Biotechnology (Santa Cruz, Calif. USA) and MBL (Medical & Biological Laboratories Co, USA), respectively. Anti-Caspase 3 & 9 pAb were purchased from Cell Signaling Technology (Danvers, Mass.).

Culture medium for all experiments was RPMI 1640 (Biological Industries, Israel), supplemented with 10% FBS (Invitrogen Life Technologies, CA), 2 mM L-glutamine, and 100 U/ml penicillin/streptomycin (Biological Industries).

A hexahistidine-tagged derivative of CTLA-4•FasL (his6CTLA-4•FasL), with the tag appended to the amino terminus, and CD40•FasL were prepared as previously described in Huang J H and Tykocinski M L (CTLA-4-Fas ligand functions as a trans-signal converter protein in bridging antigen-presenting cells and T cells. Int Immunol 2001, 13:529-539); Elhalel M D et al (CTLA-4•FasL induces alloantigen-specific hyporesponsiveness. J Immunol 2003, 170:5842-5850); and Dranitzki-Elhalel M et al (CD40•FasL inhibits human T cells: evidence for an auto-inhibitory loop-back mechanism. Int Immunol 2007, 19:355-363), respectively.

Proliferation Assays

Jurkat, Daudi or Raji cells in exponential growth phase were washed twice and re-suspended in medium at 1×106 cells/ml. 50 µl of cell suspension was added to individual wells of round-bottom 96-well tissue culture plates. CTLA-4•FasL, CD40•FasL, sFasL, CTLA-4•Ig or CD40•Fc, or combinations of the latter three were added at different concentrations. Total culture volume was 200 µl/well. In some experiments, anti-CD80 or anti-CD86 Ab were added 20 min prior to the addition of CTLA-4•FasL. In other experiments. CTLA4•Ig in PBS was added to flat-bottom 96-well plates and incubated for 1 h at 370 C and then overnight at 40 C, in order to pre-coat the plates with CTLA4•Ig. The next day, plates were washed 4 times with PBS, and 5×104 Raji cells were added to each well and incubated for 24 h. Cultures were then pulsed with 0.5 µCi of [3H]thymidine (PerkinElmer, Waltham, Mass., USA) and incubated at 37° C., 6% CO2 and 95% humidity for 18-24 hours. Cells were subsequently harvested onto glass fiber filters for scintillation counting. All proliferation assays were performed in triplicate.

Flow Cytometry

Cells were washed twice with FACS buffer (0.5% BSA/ 0.02% sodium azide in 1×PBS) and incubated on ice for 30-45 min with one of the following; FITCconjugated anti-CD40L Ab, anti-CD80 Ab, anti-CD86 Ab, anti-CD95 Ab, or their matching isotype controls, all purchased from PharMingen (San Diego, Calif., USA). Flow cytometry was performed using a FACSCalibur flow cytometer (Becton Dickinson, San Jose, Calif., USA), and data were analyzed using CellQuest software (Becton Dickinson). A total of 1×105 events were collected for each sample.

To track cells undergoing apoptosis, 1×106 Jurkat T cells or 1.5×106 Raji or Daudi B cells were incubated in 24-well plates in a total volume of 1 ml, in the presence or absence of one of the following: CTLA-4•FasL, CD40•FasL, sFasL, CTLA4•Ig or CD40•Fc or combinations of the latter three. After 4 h (T cells) or 16 h (B cells), cells were collected and washed twice with cold FACS buffer (0.5% BSA/0.02% sodium azide in 1×PBS). For detection of apoptosis and necrosis, cells were co-stained with propidium iodide (PI) and annexin-VFITC using a kit (MBL, Medical & Biological Laboratories Co, USA), according to the manufacturer's protocol. Flow cytometry was performed using a FACSCalibur flow cytometer, and data were analyzed using CellQuest software. A total of 1×105 events were collected for each sample. Whole cell lysates and Western blotting analysis Jurkat, Raji, JY or Daudi cells in exponential growth phase were washed twice, resuspended in medium at 5×106 cells/ml, and plated in 24-well plates in a total volume of 1 ml. CTLA-4•FasL, CD40•FasL, sFasL, CTLA4•Ig or CD40-Fc, or combinations of the latter three were added at different concentrations. After 90', cells were collected, washed twice with ice-cold PBS, and lysed in lysis buffer (0.5% Nonidet P-40, 50 mM Tris-HCl (pH 8.0), 100 mM NaCl, 1 mM PMSF, 1 mM sodium orthovanadate, 10 µg/ml leupeptin, and 10 µg/ml aprotinin) for 20-30 min on ice. The protein concentration of whole cell lysates was determined using the Bio-Rad Protein Assay Kit (Bio-Rad, Richmond, Calif.), according to the manufacturer's protocol. Whole cell lysates were mixed with Laemmli sample buffer (Bio-Rad) at 1:1 ratio, heated for 10 min at 95° C., and equal amounts of protein were loaded onto 10% SDSPAGE.

Following electrophoresis, gels were blotted onto nitrocellulose membranes (Schleicher & Schuell), blocked with 5% milk/PBS, and probed overnight with primary Ab. After extensive washing, blots were incubated with HRP-conjugated matching secondary Ab (Bio-Rad), and developed with enhanced chemiluminescent substrate (Sigma-Aldrich) before exposure to Xray film. Films were scanned and quantified by ImageMaster VDS-CL (Amersham Pharmacia Biotech). All membranes were re-blotted with either anti-β actin mAb or anti-GAPDH mAb to verify that similar quantities of protein were loaded on the gel.

Results

Fusion Protein-Mediated Inhibition of Cell Proliferation is Dependent on the Surface Expression of Cognate Receptors As a first step, the functionality of the component parts of the CTLA-4•FasL and CD40•FasL fusion proteins was established. To this end, malignant B (Raji, JY and Daudi) and T (Jurkat) cell lines that differ in the expression of counter-receptors for these fusion protein elements—namely B7 (CD80 and CD86), CD40 ligand (CD40L) and Fas receptor (CD95)—were used. In the case of Jurkat, two sublines that differ in their expression of CD40L (J-CD40L+ versus J-CD40L-) 26 were paired. To start, surface expression of the molecules on these various cell lines was verified by immunofluorescence and flow cytometry (FIG. 1). As expected, the B and T cell lines were positive and negative for B7 molecules, respectively, and Daudi cells expressed negligible levels of Fas receptor. The difference in CD40L expression between the J-CD40L+ and J-CD40L- T cell sublines was also confirmed.

Next, it was determined whether the differences in cognate surface receptor expression correlate with the abilities of CTLA-4•FasL and CD40•FasL to inhibit the proliferation of the tumor lines (FIG. 2A). Specifically, the different cell lines were pulsed with [3H]thymidine for 16-20 h in the presence or absence of CTLA-4•FasL, CD40•FasL, CTLA4•Ig, CD40-Fc, sFasL, or different combinations of the latter three. As expected, the proliferation of Daudi cells, which express minimal Fas receptor, was not inhibited by either of the FasL-containing fusion proteins, CTLA-4•FasL and CD40•FasL, nor by sFasL (FIG. 2A, lowest panel), highlighting the Fas-dependence of their inhibitory activity. In contrast, these fusion proteins significantly inhibited proliferation of the other two malignant B cell lines, Raji (FIG. 2A) and JY (not shown), which do express the Fas death receptor. CTLA-4•FasL was substantially more potent than sFasL and CTLA4•Ig, alone or in combination, in inhibiting proliferation of the B7-expressing malignant B cells. Indeed, CTLA4•Ig had no effect on proliferation at concentrations as high as 100 ng/ml.

Of note, CTLA-4•FasL was significantly more effective than CD40 FasL against the B cell lines (which are negative for CD40L). In fact, CD40 FasL, at concentrations up to 30 ng/ml, had no inhibitory effect on the B cell lines.

To further explore the requirement for CD40L expression on target cells for CD40•FasL's activity, advantage was taken of the Jurkat T cell derivative lines that differ in CD40L expression (J-CD40L+ versus J-CD40L-). Both of these T cell lines were inhibited by sFasL and FasL-containing fusion proteins to a greater extent than Raji B cells (FIG. 2A, upper two panels), with the JCD40L- line being the most sensitive. Interestingly, as shown previously, only cells that express CD40L (J-CD40L+) were affected by low concentrations of CD40•FasL, though at higher concentrations of CD40•FasL (e.g. >100 ng/ml), all Fas-expressing cells were inhibited to some degree (not shown).

Given that T cells were highly sensitive to all forms of sFasL, it was not possible to use them as B7-negative controls for establishing the requirement for B7 surface expression in CTLA-4•FasL's activity. Consequently, an Ab blocking experiment was performed using B7-positive B cells as targets. In particular, CTLA-4•FasL's inhibitory effect in the absence or presence of antagonistic Ab against CD80 and CD86 (FIG. 2B) was compared. Anti-CD80 blocking Ab (0.5 or 1 µg/ml) significantly attenuated the inhibitory effect of CTLA-4•FasL (30 ng/ml). In contrast, anti-CD86 Ab, at the same concentrations, had no effect on CTLA-4•FasL inhibition of Raji cell proliferation. The addition of the two blocking Ab in combination completely abolished CTLA-4•FasL's inhibitory effect. Taken together, these data indicate that CTLA-4•FasL and CD40•FasL exhibit maximal inhibitory potency when the target malignant lymphoid lines express cognate counter-receptors for both domains of each fusion protein.

Fusion Protein-Mediated Induction of Apoptosis is Dependent on the Surface Expression of Cognate Receptors Previous studies have established that both CTLA-4•FasL and CD40•FasL induce their inhibitory effect via Fas-mediated apoptosis. It was then considered whether apoptosis induction by these fusion proteins parallels proliferative inhibition in being more efficient when target cells co-express surface molecules that can bind both ends of the respective proteins. To this end, the same set of malignant cell lines were incubated for 4 (T cells) or 16 (B cells) hours in the presence or absence of CTLA-4•FasL, CD40•FasL, CTLA4-Ig, CD40-Fc, sFasL, or different combinations of latter three. At the end of the treatment period, cellular apoptosis and necrosis were assessed using Annexine/PI staining and flow cytometry. Again as expected, FasL-containing fusion proteins or sFasL had no effect on Daudi B cells lacking Fas receptor, and neither CTLA-4•Ig or CD40-Fc induced apoptosis in the Daudi cells (FIG. 3A, B). By contrast, and as was the case in the proliferation assay, CTLA-4•FasL significantly increased the percentage of apoptotic or necrotic Raji cells at 16 h (FIG. 3A, B). Again, more apoptosis was detected when Raji cells were incubated with CTLA-4•FasL, as opposed to sFasL, CTLA-4-Ig, or a combination of the latter two. No significant apoptosis of Raji cells was induced by CD40•FasL (FIG. 3A, C).

When Jurkat T cells (either J-CD40L+ or J-CD40L−) were incubated with CTLA-4•FasL, significant apoptosis ensued, though J-CD40L+ were less affected than J-CD40L− (FIG. 3A, C). The same difference in susceptibility to apoptosis induction between these paired cells lines was evident when sFasL or the anti-Fas Ab CH11 (not shown) was used. However, when the Jurkat cell lines were incubated in the presence of CD40•FasL, significant apoptosis could be detected only in J-CD40L+ cells, despite the fact that sFasL was more potent in inducing apoptosis in J-CD40L− cells (FIG. 3A, C). This set of experiments highlights the functional importance of both ends of each of the respective fusion proteins for efficient apoptosis induction.

Both Pro-Apoptotic and Anti-Apoptotic Pathways are Affected by CTLA-4•FasL and CD40•FasL The possibility that the apoptosis-inducing activity of CTLA-4•FasL and CD40 Fas may not be solely reliant on triggering of the Fas death receptor was then considered. To test this hypothesis, the T and B cell lines were incubated for 90-180 min with CTLA-4•FasL, CD40•FasL, sFasL, CTLA-4•Ig, CD40 or combinations of the latter three. At the end of the incubation period, whole cell lysates were evaluated by immunoblotting for expression of the anti-apoptotic protein cFLIP, caspase 8 (as a marker of the extrinsic pathway), caspase 9 (as a marker of the intrinsic, mitochondrial pathway), and caspase 3. Of note, both the pro-caspase forms (not shown) and the cleaved, active caspase forms were examined. A representative experiment is shown in FIG. 4A, and the summary of 3 independent experiments performed with the different cell lines is shown in FIGS. 4 B-D.

Figure 4A:
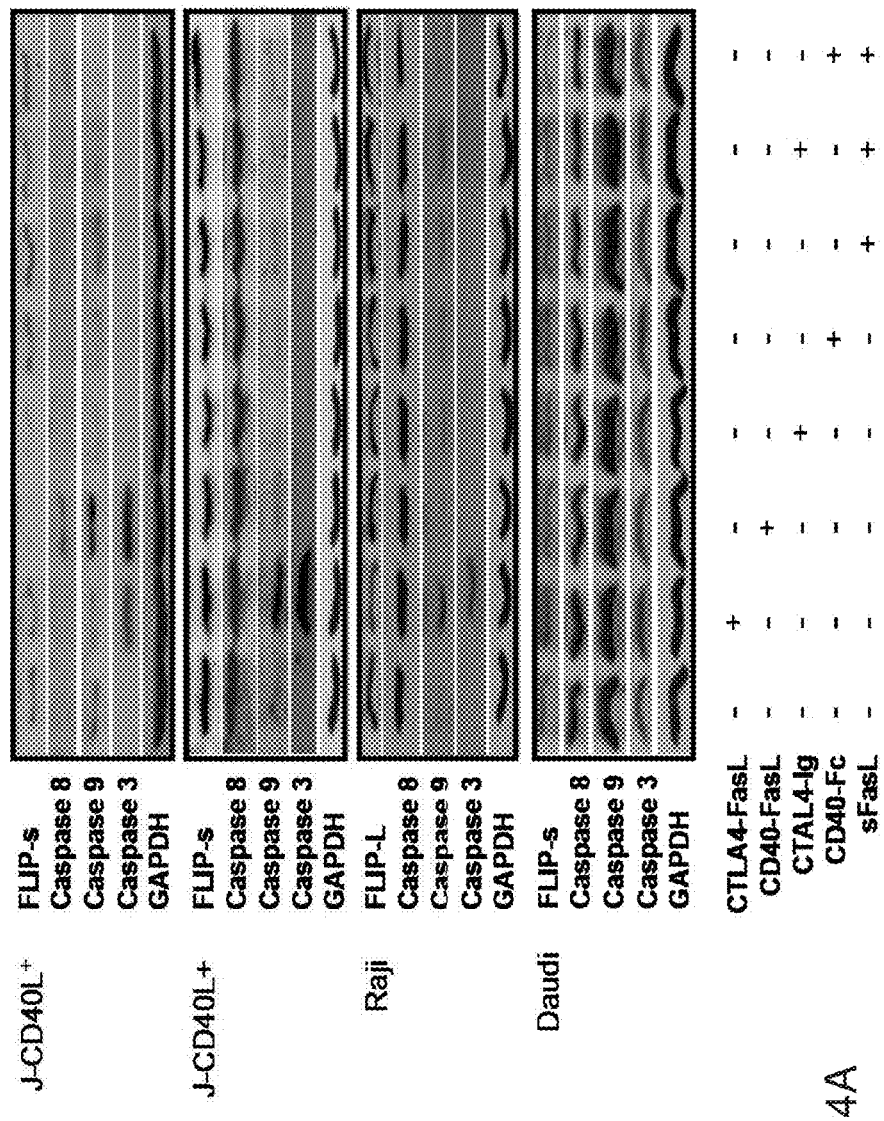
FIG. 4. CTLA-4•FasL and CD40-FasL each affects both apoptotic and anti-apoptotic signaling pathway elements. J-CD40L+J-CD40L−, Raji and Daudi cells were incubated in the presence or absence of either CTLA-4•FasL, CD40•FasL, sFas, CTLA-4•Ig, CD40-Fc or their combinations as indicated, for 90 min. Cells were collected, whole cell lysates were fractionated on 10% SDS-PAGE, and immunoblotted with the indicated Ab. A. Representative immunoblots for Jurkat malignant T cell lines and Raji and Daudi malignant B cell lines. Data shown is a representative experiment of at least three independent experiments for each cell line. B-C. Summary of three independent experiments with the indicated Ab for Raji (B) and Jurkat (C) cell lines. The active forms of caspases 3, 9 and 8 are shown. Data were normalized against GAPDH. Expression of proteins in cells incubated in medium (control) were considered as 100%. Data are presented as mean±SD. *p<0.05 vs. medium, **p<0.01 vs. medium.

The expression of the different caspases in the Daudi B cell line (with negligible Fas receptor) did not change after incubation with the FasL-containing proteins (FIG. 4A). Furthermore, no change was found when Daudi cells were incubated with CTLA-4•Ig, CD40-Fc or a combination of the latter with sFasL (FIG. 4A). In contrast, B cell lines co-expressing B7 molecules and Fas receptors yielded an entirely different picture. After 90 or 180 minutes of incubation in the presence of CTLA-4•FasL, cFLIPL expression was abrogated, and a clear increase in the activated (cleaved) forms of two of the caspases (9 and 3) was observed. Since caspase 8 is found mainly in its active, cleaved form in these cells, even when Fas receptor is not triggered and cFLIP base levels are very low, another malignant B cells line, JY, also co-expressing B7 molecules and Fas receptor, was considered.

Figure 4C:
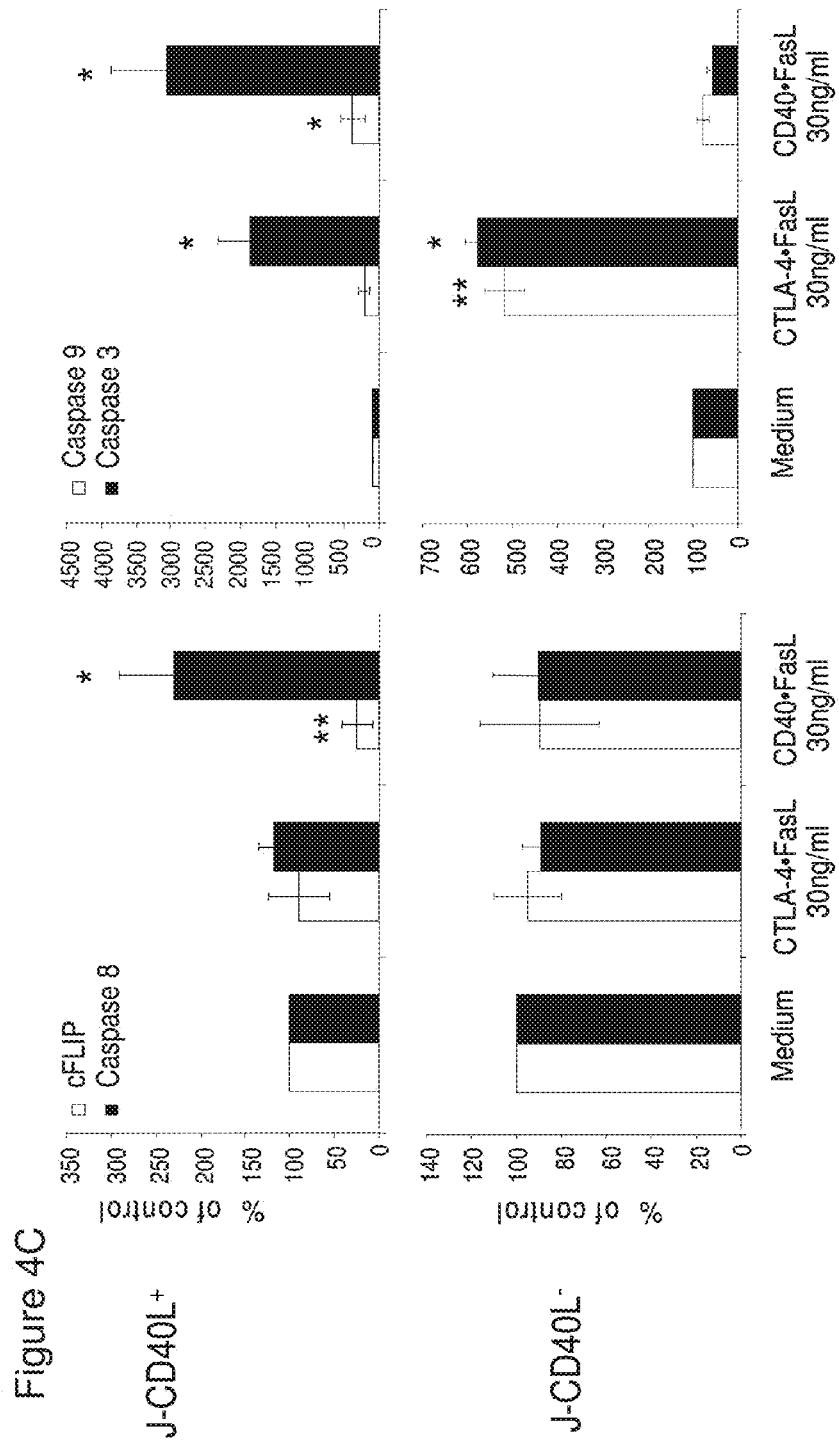
Figure 5A:
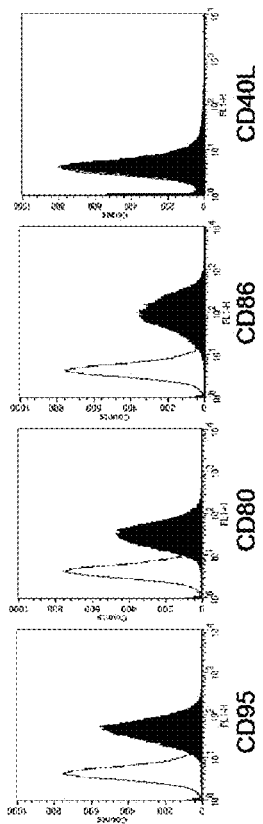
FIG. 5. CTLA4•FasL increases apoptotic signals and decrease the anti-apoptotic protein cFLIP in JY malignant B cells. JY cells were incubated in the presence or absence of either CTLA-4•FasL, CD40•FasL or anti-Fas Ab (CH11) for 90 min. Cells were collected, whole cell lysates were fractionated on 10% SDS-PAGE, and immunoblotted with the indicated Ab. A. Representative immunoblots of three independent experiments for each cell line. B Summary of three independent experiments of JY malignant B cell lines with cFLIPs and anti-caspase 8 Ab C Summary of three independent experiments of JY malignant B cell lines with anti-caspase 9 and 3 Ab. Expression of proteins in cells incubated in medium (control) were considered as 100%. Data are presented as mean±SD. *p<0.05 vs. medium, **p<0.01 vs. medium.
Figure 5B:
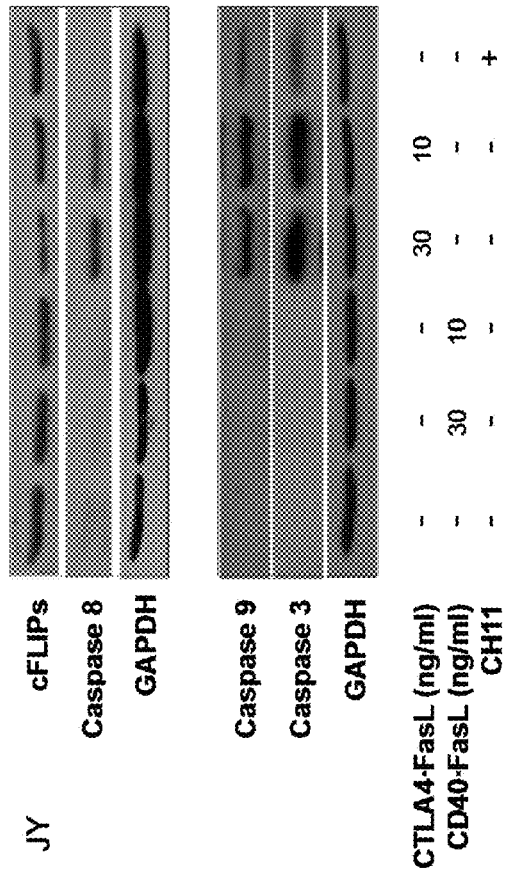

When incubated with CTLA-4•FasL, there was a clear decrease in cFLIP abundance and a significant increase in the activated forms of caspases 3, 9, and 8 (FIGS. 5A-C). In contrast, CD40•FasL, sFasL, CTLA-4•Ig, or CD40-Fc had no effect on cFLIP expression or caspase activation in either of the malignant B cell lines (FIGS. 4 and 5).

The next focus was on CD40 FasL with an appropriate cell target, J-CD40L+. When the J-CD40L+ and J-CD40L− T cell lines were incubated with CTLA-4•FasL or CD40•FasL, the pattern expression of apoptotic and anti-apoptotic protein expression was distinctly different from that seen with the B cell lines (FIG. 4A, upper two panels; FIG. 4C). In both Fas-expressing Jurkat cell lines, CTLA-4•FasL and CD40•FasL each activated the caspase cascade, showing increased abundance of the activated forms of caspase 9 and 3.

Caspase 8 appears in its activated form in these cell lines. No change in cFLIP abundance was noted. However, J-CD40L+ cells, though less sensitive to CTLA-4•FasL than J-CD40L− (as one reflected in the lesser increase in the activated forms of caspase 9 and 3), responded to CD40•FasL treatment with a significant decrease in cFLIP abundance, and additional activation of caspases 8, 3 and 9. CD40•FasL was more potent in doing so than CD40-Fc, sFasL or a combination of the two. Taken together, these experiments establish that CTLA-4•FasL and CD40•FasL each has dual and reinforcing effects on both apoptotic (caspase) and anti-apoptotic (cFLIP) pathways.

Figure 6B:
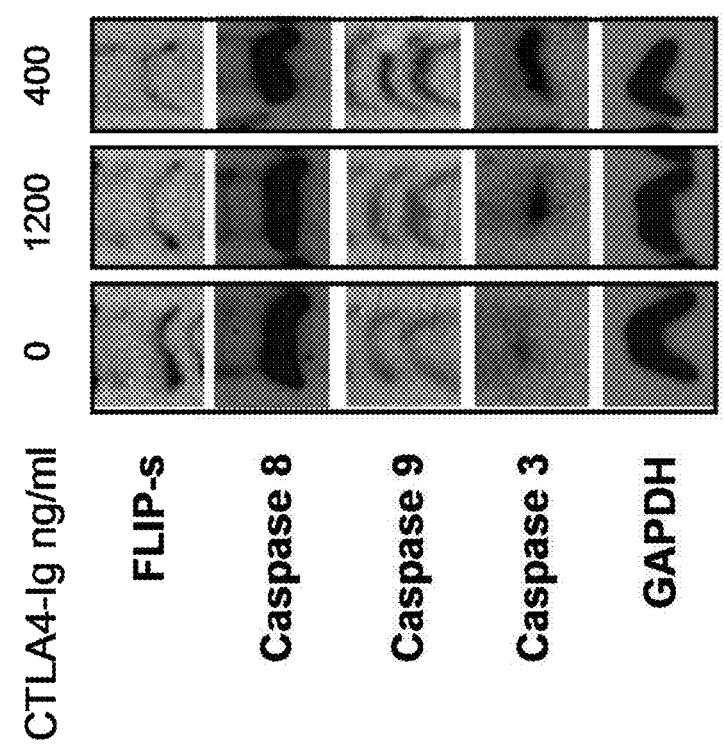
FIG. 6. CTLA-4•Ig reduces proliferation of B7-expressing cells and affects their expression of caspases and cFLIP. A. Raji malignant B cells were incubated in the presence or absence of CTLA-4•FasL on flat-bottom 96-well plates that were pre-incubated with CTLA-4•Ig overnight. Assays were performed in triplicate. Cells were pulsed with [3H]thymidine, incubated for 24 h and then evaluated for [3H]thymidine incorporation. [3H]thymidine incorporation of cells in medium (control) was designated as 100%, and the rest are presented as % of control, mean±SD. *P<0.05 versus control, **P<0.01 versus control. Data shown are a summary of three independent experiments. B-C. Raji cells were incubated on 24-well plates pre-coated with CTLA-4•Ig for 90 min. Cells were collected, whole cell lysates were fractionated on 10% SDS-PAGE, and immunoblotted with the indicated Ab. B. Representative immunoblots with the indicated Ab. C. Summary of three independent experiments. The active forms of caspases 3, 9 and 8 are shown. Data were normalized against GAPDH. Expression of proteins in cells incubated in medium (control) were considered as 100%. Data are presented as mean±SD. *p<0.05 vs. medium.

CTLA-4•Ig inhibits proliferation of a B cell line and decreases cFLIP levels. One possible explanation for the special properties of the fusion proteins, with unique impact on anti-apoptotic signaling, is back-signaling through the non-Fas surface counter-receptors for the fusion protein components. Indeed back-signaling through the 'costimulatory ligands' B7 (on antigen-presenting cells) and CD40L (on T cells) has been documented by others. It was therefore considered whether the exceptional potency of the CTLA-4•FasL and CD40•FasL fusion proteins might be explained, at least in part, by backsignaling through B7 and CD40L, respectively, occurring simultaneously with Fas receptor triggering. For that purpose, Raji B cells were treated with CTLA-4•FasL for 24 h, in the presence or absence of plate-bound CTLA-4•Ig, and proliferation was assessed. As shown in FIG. 6A, plate-bound CTLA-4•Ig alone significantly inhibited Raji cell proliferation. CTLA-4•FasL-mediated inhibition of Raji cell proliferation was diminished in the presence of plate bound CTLA-4•Ig, suggesting interference with CTLA-4•FasL binding to B7 (FIG. 6B). Significantly, plate-bound CTLA-4•Ig, like CTLA-4•FasL, reduced cFLIP expression in Raji cells and increased the expression of caspases 9 and 3 in them (FIG. 6C). These findings suggest that CTLA-4•Ig can deliver an inhibitory back-signal to malignant B cells and reduce anti-apoptotic cFLIP in them.

It was considered whether CD40•FasL can mediate similar back-signaling through CD40L. In order to test this possibility, J-CD40L+ cells were incubated with CD40-Fc. CD40-Fc increased J-CD40L+ proliferation by ~20% (not shown). However, no effect on the expression of the apoptotic and antiapoptotic proteins was observed when CD40-Fc was used at concentrations up to 1200 ng/ml (data not shown).

Discussion

In this study, the unique functional properties of two fusion proteins, CTLA-4•FasL and CD40•FasL, as inducers of apoptosis in malignant lymphoid cell lines have been considered, focusing on relevant intracellular signaling cascades. Without wishing to be limited by a single hypothesis or a closed list, these findings include: 1) CTLA-4•FasL and CD40•FasL induce death in Fas receptor-expressing malignant lymphoid lines of both B and T lineages; 2) CTLA-4•FasL induces apoptosis in B7-expressing B cell lines more potently than does CD40•FasL; 3) CD40•FasL induces apoptosis in CD40L-expressing J-CD40L+ T cells in a CD40L-dependent fashion; 4) CTLA-4•FasL lowers cFLIP expression and activates the caspase cascade in cells co-expressing both B7 and Fas receptor at their surfaces; 5) CD40 FasL lowers cFLIP expression and activates the caspase cascade in cells co-expressing both CD40L and Fas receptor, and 6) CTLA-4•FasL and CD40•FasL are each more effective in inducing apoptosis than either of their component parts, alone or in combination.

Taken together these findings affirm the higher order functionality of these unique fusion proteins, and suggest that they may have special advantages for inducing apoptosis in malignant lymphoid cells, by coordinately affecting apoptotic and anti-apoptotic pathways. One of the mechanisms enabling malignant cells to escape apoptosis, and thereby remain refractory to treatment, is up-regulation of anti-apoptotic proteins. FLIP, expressed either intrinsically (as cFLIP) or extrinsically (as vFLIP), has been implicated as a key anti-apoptotic protein in several malignant lymphomas. It has been previously shown that CTLA-4•FasL prevents the up-regulation of cFLIP expression that normally accompanies T cell activation. By abrogating up-regulation of this anti-apoptotic protein, CTLA-4•FasL is able to induce apoptosis in activated T cells at an earlier phase than does sFasL. The present study extends this functional feature of CTLA-4•FasL to transformed cells.

For most of the cell lines studied here (that is, J-CD40L+, J-CD40L– and JY cells), reduction in cFLIP expression was correlated with activation of caspases 3, 8, and 9. Caspase 8 activation is dependent on its binding to the death complex FADD. This binding leads to activation of caspase 3, and Bid, that in turn results in cytochrome c and caspase 9 activation. Activation of caspase 9 then leads to more caspase 3 activation and effective apoptosis. The ability of cFLIP proteins to inhibit caspase 8 activation, by competing with caspase 8 for binding to the death complex FADD, is well-established.

There are contradictory data in the literature concerning the role of the two splice variants of cFLIP:cFLIP short (cFLIPs) and cFLIP long (cFLIPL). cFLIPL's role in the system appears to be more complicated, with data indicating that high levels of expression lead to apoptosis, whereas moderate levels result in the opposite, that is, inhibition of Fas-mediated apoptosis in vitro and in vivo. However, data are clearer in the case of cFLIPL under-expression, in that selective silencing of cFLIPL mRNA augments caspase 8 recruitment, activation, processing and release from the death complex and hence enhanced apoptosis. Only the cFLIPL splice variant was detected in the Raji B cell line, and CTLA-4•FasL, able to bind to both B7-1 (CD80) and Fas receptor (CD95) on these cells, decreased expression of this cFLIP isoform. Significantly, despite the constitutive expression of the activated form of caspase 8 in these Raji cells. CTLA-4•FasL-driven cFLIPL reduction was correlated with activation of caspases 9 and 3 and effective induction of apoptosis. Without wishing to be limited by a single hypothesis, reduction of cFLIP by CTLA-4•FasL and CD40•FasL may lead to both pro-apoptotic and anti-proliferative effects in transformed lymphoid cells.

By chimerizing FasL to CTLA-4 and CD40, one creates intriguing molecular bridging possibilities. Transformed B cells introduce a new scenario wherein the same fusion protein can potentially bridge the counter-receptors being co-expressed on the same cell. Intercellular and intracellular bridging by both CTLA-4•FasL and CD40•FasL are certainly not mutually exclusive, and one can envision both taking place in the context of local tumor growth.

The cis loop-back auto-signaling mechanism may lead to more effective inhibition on more than one basis. First, the fusion proteins serve to tether FasL to membranes, via either CTLA-4:B7 binding on B cells or CD40:CD40L binding on T cells. The potency of surface-anchored FasL has been clearly established in the context of exogenously-introducing it onto APC surfaces to generate deletional APC 56-59. One would thus expect fusion protein-tethered FasL to be highly functional in an auto-signaling mode as well. Second, both CTLA-4•FasL and CD40•FasL have the potential to act as dual-signaling agents by triggering neighboring counter-receptors on the same cell surface.

Back-signaling through the B7 molecules CD80 and CD86 has been described for B cells 23, leading to proliferative inhibition of B cells in the case of CD80 and the opposite for CD86. Since CTLA-4 has higher avidity for CD80, one might expect the CD80-related effect to dominate for CTLA-4•FasL. Data here showing that CTLA-4•Ig inhibits proliferation of CD80-expressing Raji cells is consistent with this back-signaling function.

Back-signaling has also been demonstrated for CD40L on T cells, and thus could also contribute to CD40•FasL's observed efficacy. In the case of CD40•FasL, but not CD40-Fc, the CD40 moiety is being presented in a cellbound mode (via FasL:Fas anchoring), and with the likelihood of being in a trimer or two-trimer configuration (versus the presumed CD40-Fc dimer).

Indeed, it has been shown that CD40-Fc has lower affinity for CD40L than do oligomers of CD40, and this higher affinity is accompanied by stronger biological activity. Taken together, but without wishing to be limited by a single hypothesis, these various data suggest that not only can each of CTLA-4•FasL and CD40•FasL deliver dual signals on the same cell, but in both instances, the Fas signaling can be potentiated by backsignaling through the other counter-receptor (B7-1 or CD40L).

Of note, CTLA-4•FasL was found to be a potent inducer of apoptosis in Jurkat T cells, even though these cells are negative for B7 proteins. This likely reflects their overall higher susceptibility to soluble FasL-mediated apoptosis, as evidenced by their high sensitivity (especially the J-CD40L– subline) to sFasL and agonistic anti-Fas Ab (CH11; data not shown).

The present study highlights the functional richness of appropriately configured fusion proteins. The CTLA-4•FasL and CD40•FasL fusion proteins modulate both normal and transformed lymphoid cells, serve to bridge molecules intercellularly and intracellularly, set up artificial cis loop-back autosignaling loops, and deliver dual-signals that are reinforcing. Both of these proteins can down-modulate anti-apoptotic cFLIP isoforms, an effect that serves to potentiate the FasL pro-apoptotic signal that these same proteins deliver. Thus, one can leverage fusion proteins to simultaneously deliver a death signal and sensitize the cells to it.

Example 2—Clinical Trial of a Chimeric Protein for Treatment of a Hematological Malignancy A phase I trial of a chimeric protein (therapeutic agent) as described herein to subjects with a hematological malignancy selected from the group consisting of lymphoma, multiple myeloma and a leukemia as recited herein, may be designed to evaluate both effect on disease progression and possible toxicity. Subjects with a suspected hematological malignancy may be enrolled after positive diagnosis of the hematological malignancy as is well known in the art.

Treatment may be provided as a single therapeutic or in combination with accepted treatments. For example, treatment strategies for multiple myeloma are reviewed in Rajkumar et al., 2002, Mayo Clin. Proc. 77:814, hereby incorporated by reference in its entirety). Recognition of acute or unusual progression of the disease may halt administration of therapeutic agent.

Initial subjects receive a suitable dosage of therapeutic agent, administered for example as a 1 hour intravenous infusion or as appropriate, alone or in combination with one or more other known agents as could be selected by one of ordinary skill in the art. Given adequate tolerance, the dose will be increased stepwise in subsequent subjects. Additionally, the method for administration may be changed to bolus injection.

Toxicity of therapeutic agent is evaluated in subjects according to the World Health Organization Toxicity Criteria: blood pressure, temperature and heart rate are monitored every 10 minutes during infusion, then every hour for 3 hours and finally every 3 hours for 24 hours. Hematologic, renal and liver function tests are conducted every other day for one week and on day 15, 30, 60 and 120 post injection.

Serum and/or tissue samples are obtained once a week for two months so that the effects of the therapeutic agent may be determined by methods known in the art, e.g., change serum concentration of M protein, change in hemoglobin value, presence/regression of lytic bone lesions etc. Pathologic studies will assess treatment effect on tissue damage associated with the hematological malignancy.

Example 3—Effect on Tumor Cell Lines

Materials and Methods.

Unless otherwise stated, all chemicals were obtained from SIGMA (Israel). DMEM medium, FBS, PBS, Trypsin-EDTA, penicillin, streptomycin and L-Glutamine were obtained from Biological Industries (Beit Haemek, Israel).

Cell Lines.

Raji (EBV transformed B cell lymphoma line), JY (EBV transformed B cell lymphoma line), Daudi (EBV transformed B cell lymphoma line) RPMI 8226 (human multiple myeloma cell line), HL60 (Human promyelocytic leukemia cells) were purchased from ATCC (USA). SK-HEP-1 (HTB-52; liver adenocarcinoma cell line) was purchased from ATCC (USA). HepG2. Huh7 hepatocellular carcinoma cell lines, originally from the ATCC, were kindly provided by the Hepatology Unit, Hadassah Hebrew University Medical Center in Jerusalem, Israel. Unless otherwise stated, all cell lines were grown in 10% FBS DMEM supplemented with 10 U/ml penicillin, 0.1 mg/ml streptomycin and 292 µg/ml L-Glutamine. All cell lines were cultured at 37° C. in 6% $CO_2$ and cultures were tested periodically for *mycoplasma* contamination using EZ-PCR *mycoplasma* test kit (Biological Industries).

Activity Assay.

To assess KAHR-102 (CTLA4-FasL) activity, $0.2 \times 10^6$ cells/ml were seeded as triplicates in 96-well plates (NUNC, Roskilde, Denmark) and cultured with or without varying concentrations of the histidine tagged version of KAHR-102 (his6CTLA4-FasL), Cells were incubated with the indicated protein concentration for 24 h at 37° C. in 6% $CO_2$, and cell viability was evaluated using MTS assay (Promega, Madison, USA).

Flow Cytometry.

To assess apoptosis, $0.2 \times 10^6$ cells/ml were seeded as duplicates in 24-well plates (NUNC) and incubated with or without varying concentrations of his6CTLA4-FasL (KAHR-102), soluble FasL, CTLA4-Fc or the latter in combination for 24 h. Cells were then harvested, and apoptotic cells were detected by flow cytometric analysis, using the AnnexinV/PI MEBCYTO Apoptosis Kit (MBL, Nagoya Japan), according to the manufacturer's protocol. 20,000 events per sample were counted using a FACSCalibur flow cytometer (Becton Dickinson, San Jose, Calif., USA), and data were analyzed using CellQuest software (Becton Dickinson).

To examine expression of Fas receptor and the B7 molecules, CD80 and CD86, in the different cell lines, cells were retrieved, washed in staining buffer (PBS containing 1% BSA and 0.1% sodium azide), and stained with phycoerythrin-labeled mAb with specificity for the above mentioned molecules or the relevant control Abs, at concentrations recommended by the manufacturer (eBioscience). Flow cytometry was performed using a FACSCalibur flow cytometer (Becton Dickinson), and data were analyzed using CellQuest software (Becton Dickinson). A total of 20,000 events were collected for each sample.

Statistical Analysis.

Data are presented as means±SD. Statistical comparison of means was performed by a two-tailed unpaired Student's t test. Differences with a p<0.05 were considered statistically significant.

Establishment of Tumor Xenografts.

Athymic BALB/c nu/nu nude male mice (Harlan. Israel), 4-6 weeks of age, maintained under defined flora conditions at the Hebrew University Pathogen-Free Animal Facility will be used. All experiments were approved by the Animal Care Committee of the Hebrew University. Raji, JY or RPMI 8226 grown to 80% confluence, harvested, washed with PBS, and injected subcutaneously ($2 \times 10^7$/mouse) into the right flanks of mice or intraperitoneal. Once palpable, tumors will be measured for their widths and lengths using a micro-caliper for the subcutaneous tumors, and tumor volumes were calculated (w2× length/2), or, for the intraperitoneal tumors, abdominal diameter will be measured, and mice will be weighted. Mice will treated daily with subcutaneous injections of his6CTLA4-FasL (KAHR-102), (200 µg) for 8 days. If tumor will re-grow or re-appear, another treatment will follow in two weeks. Control groups will be injected with similar volumes of the his6CTLA4-FasL (KAHR-102) dilution buffer. Tumor volumes will monitored for approximately a 3 month, or until tumor size exceeded the threshold requiring sacrifice of the animal. At the end of experiments, mice will be sacrificed, and tumors will be harvested, measured and weighed, and analyzed.

Results

Figure 7:
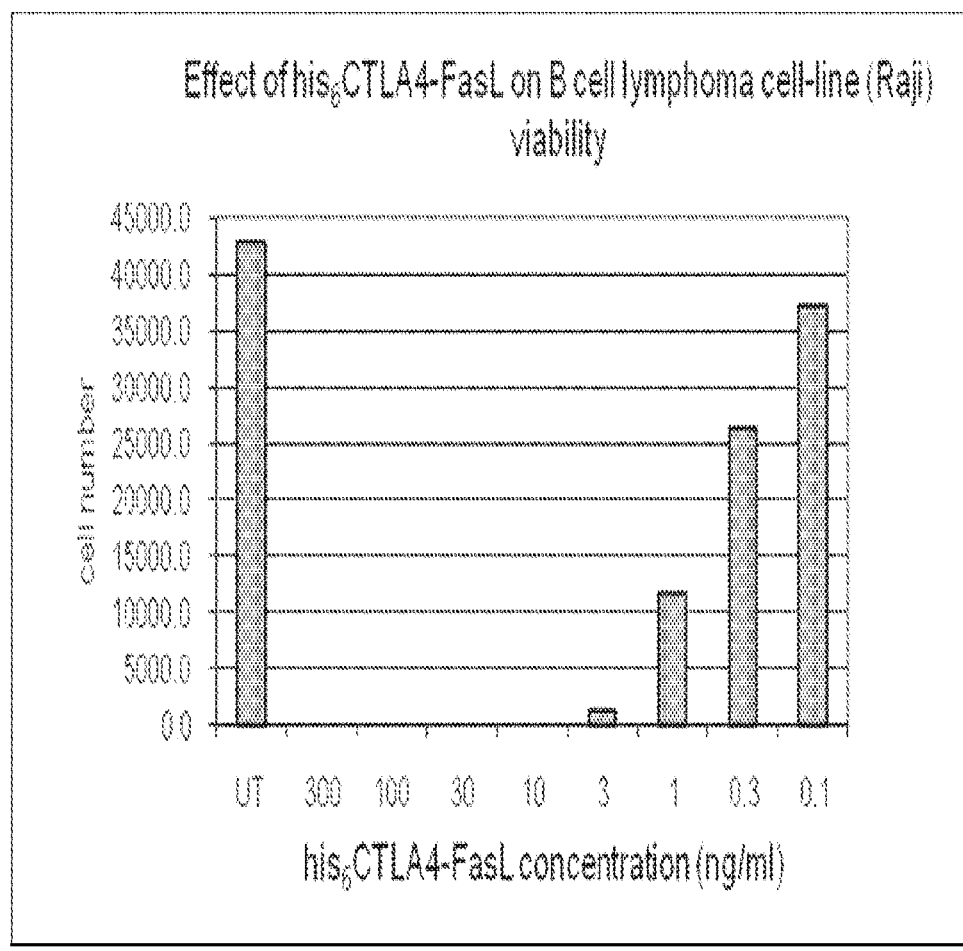
FIGS. 7 and 8 show that CTLA4-FasL induces death of both Raji and JY, B-cell lymphatic cancer cell lines, in a dose-dependent fashion.
Figure 8:
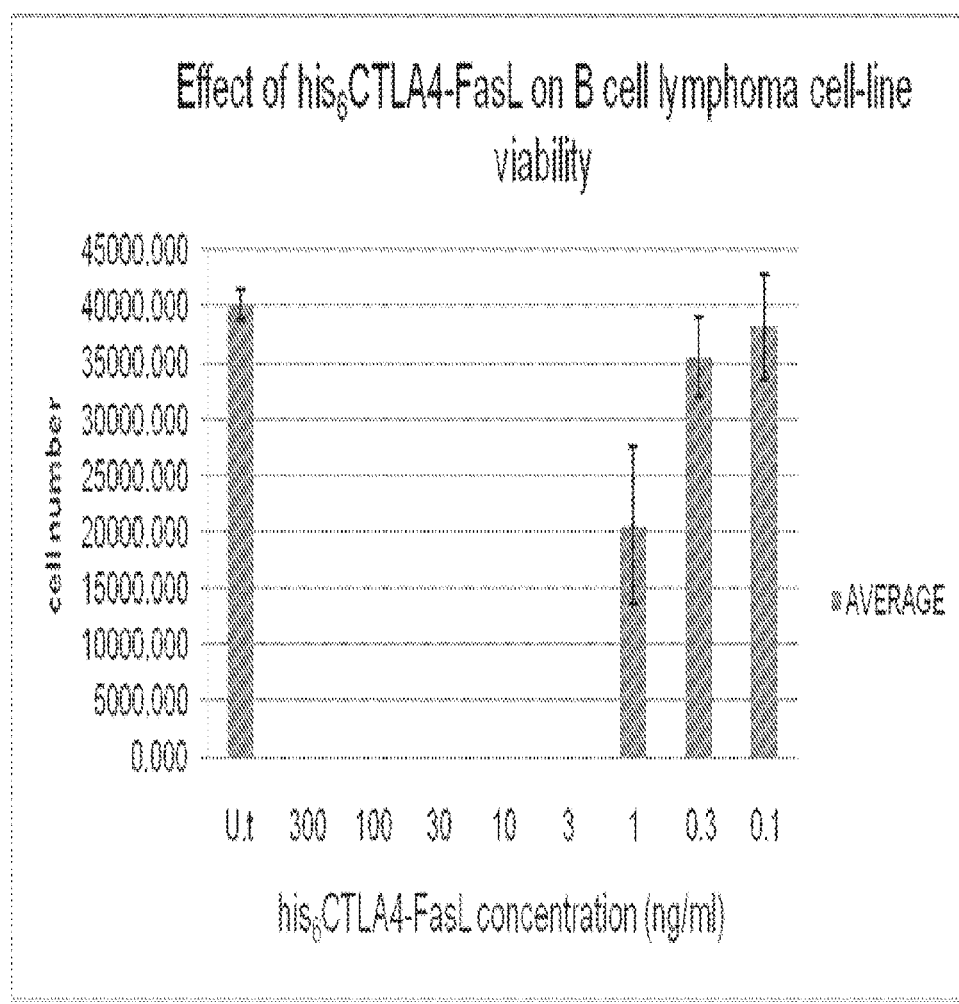

CTLA4-FasL's cytotoxic activity was evaluated against different lymphoma cells. As shown in FIGS. 7 and 8, CTLA4-FasL induces death of both Raji and JY, both of which are B-cell lymphatic cancer cell lines, in a dose-dependent fashion. Of note, significant cell death was detected at a concentration as low as 0.1 ng/ml, corresponding to an EC50 of 0.4 nmol/l. Cell death was detected at 24 h, and was more robust at 48 h, with almost no live cells detectable at 3 ng/ml CTLA4-FasL. Importantly, primary B cells taken from healthy volunteers were resistant to CTLA4-FasL's toxic activity (not shown).

Figure 9:
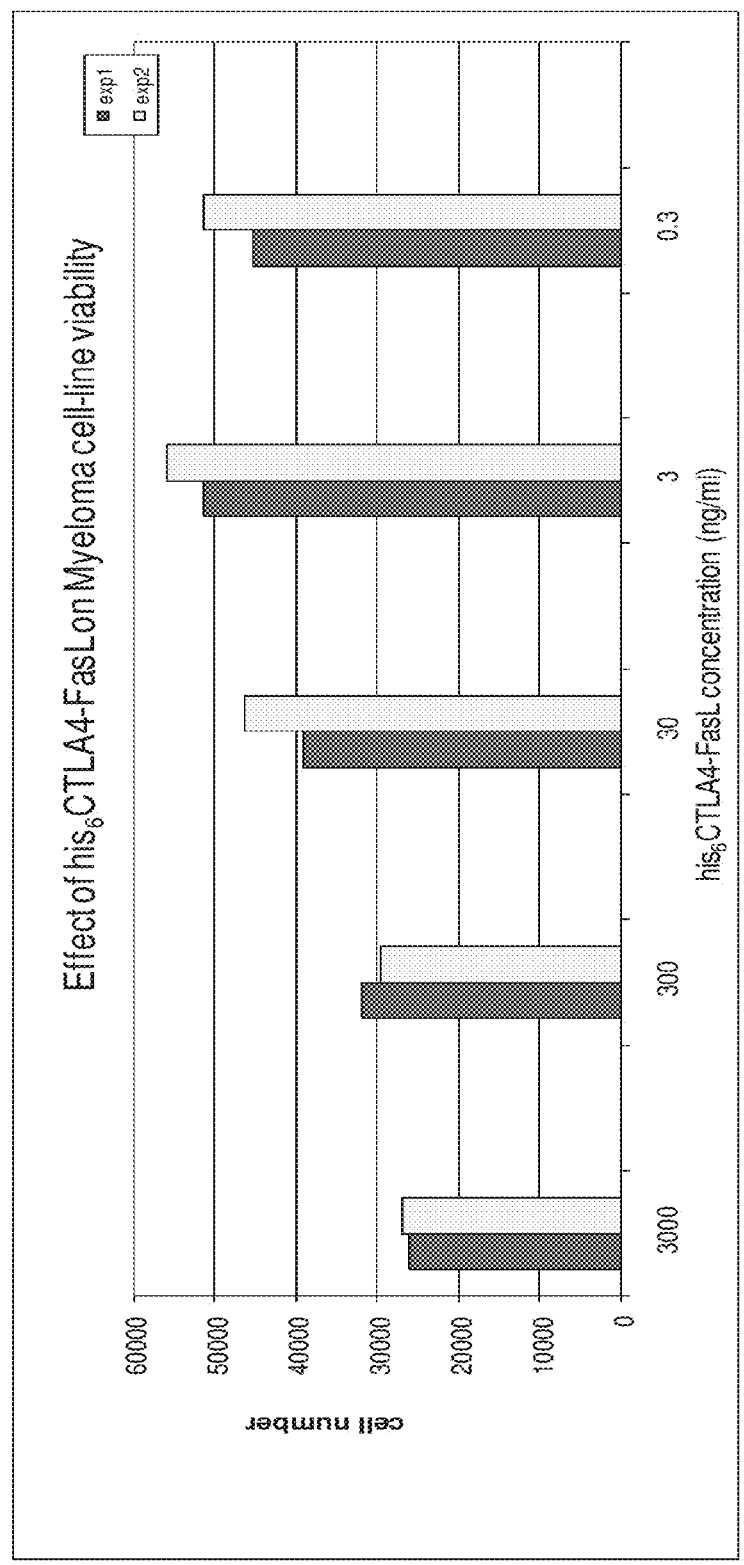
FIG. 9 shows the effect of CTLA4-FasL on RPMI 8226.
Figure 10:
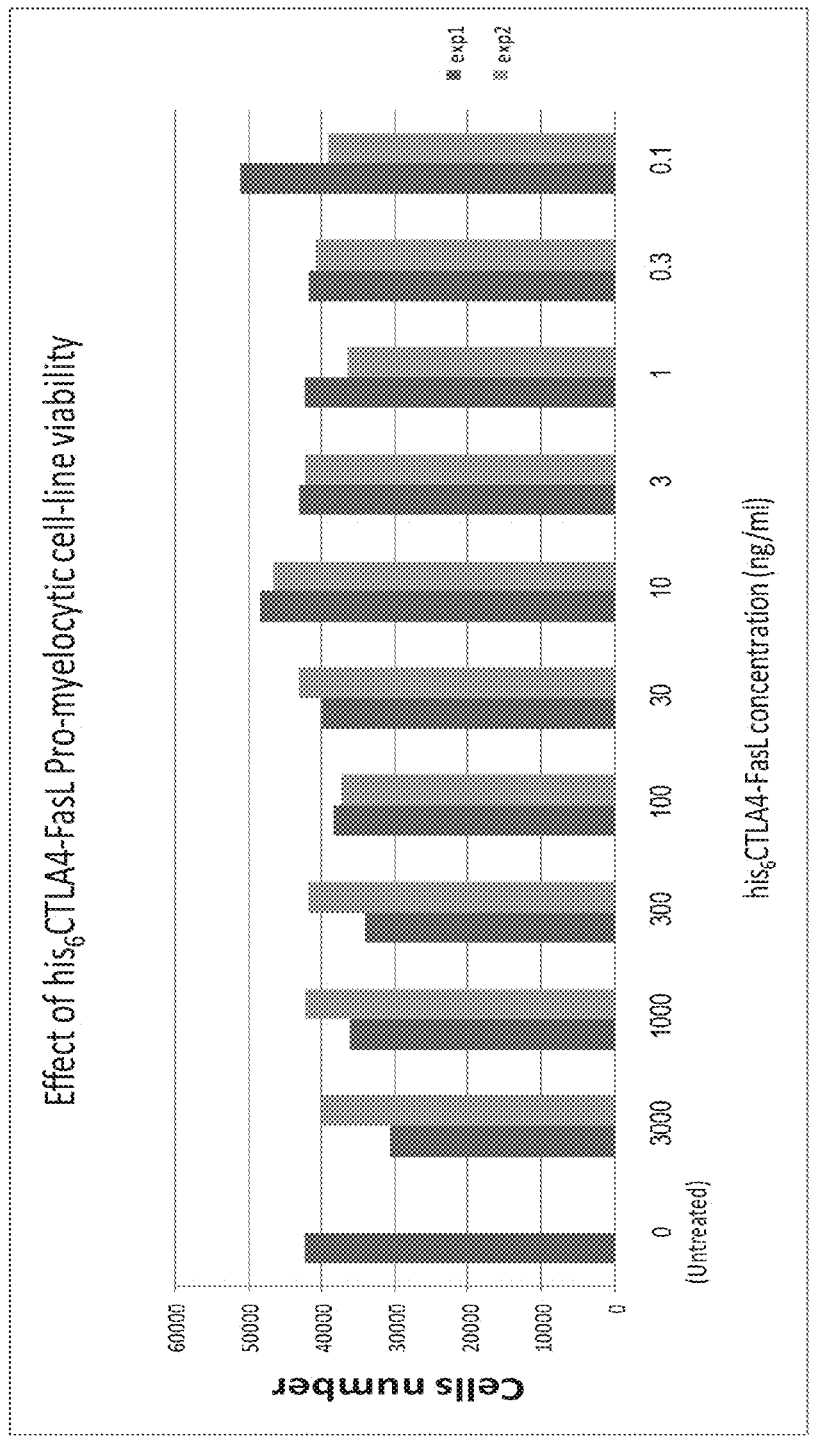
FIG. 10 shows the effect of CTLA4-FasL on promyelocytic leukemia cells.
Figure 11:
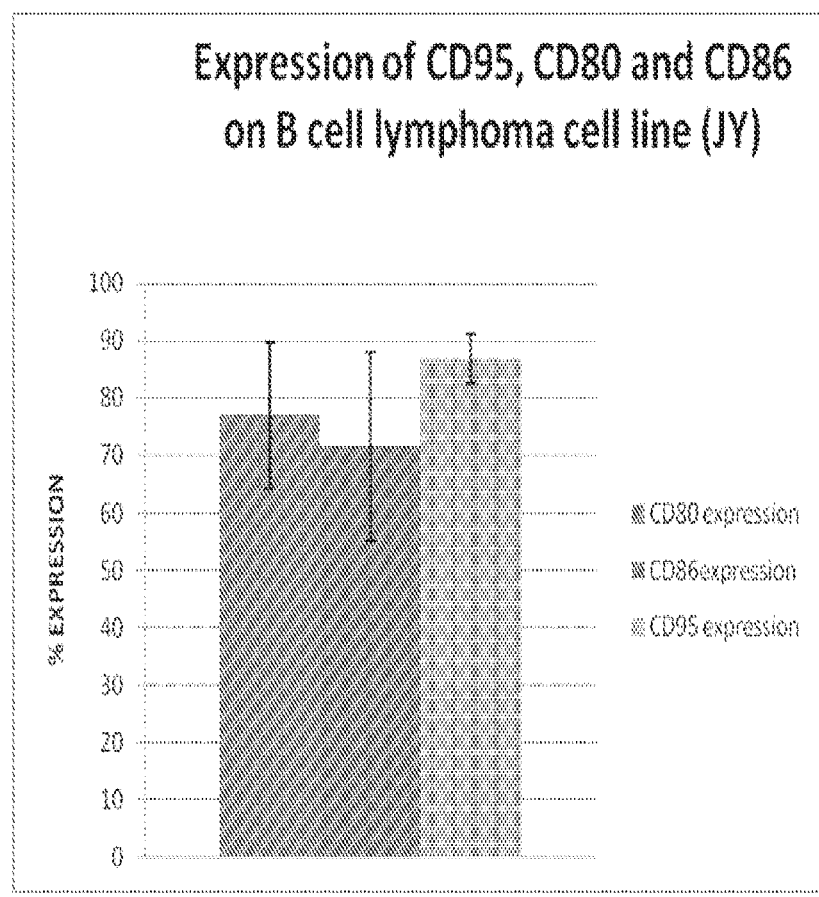
FIGS. 11-14 relate to the surface expression of CD80 and CD86, which bind CTAL4, and the expression of CD95 (Fas receptor, which binds FasL), in various cell lines.
Figure 12:
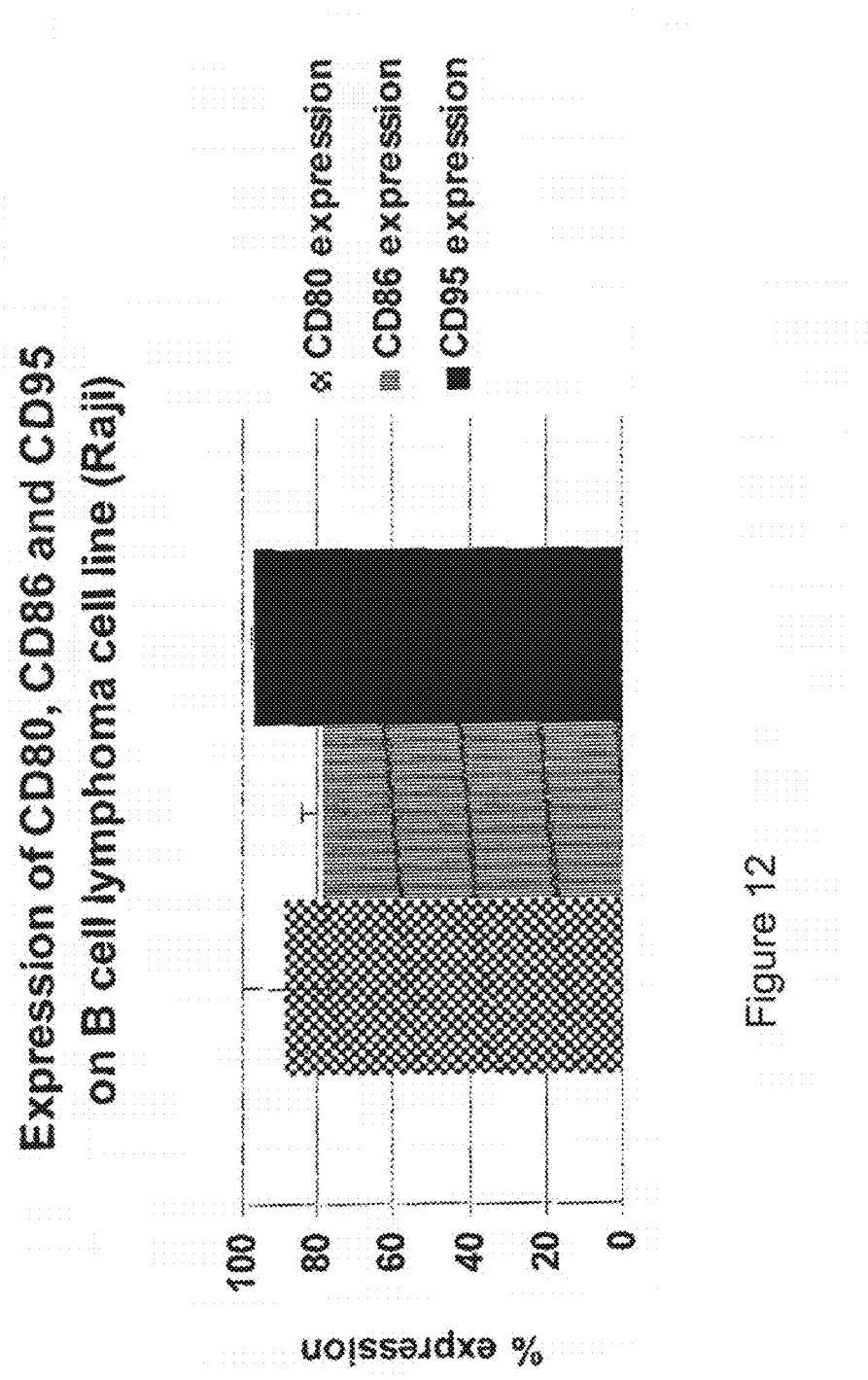
Figure 13:
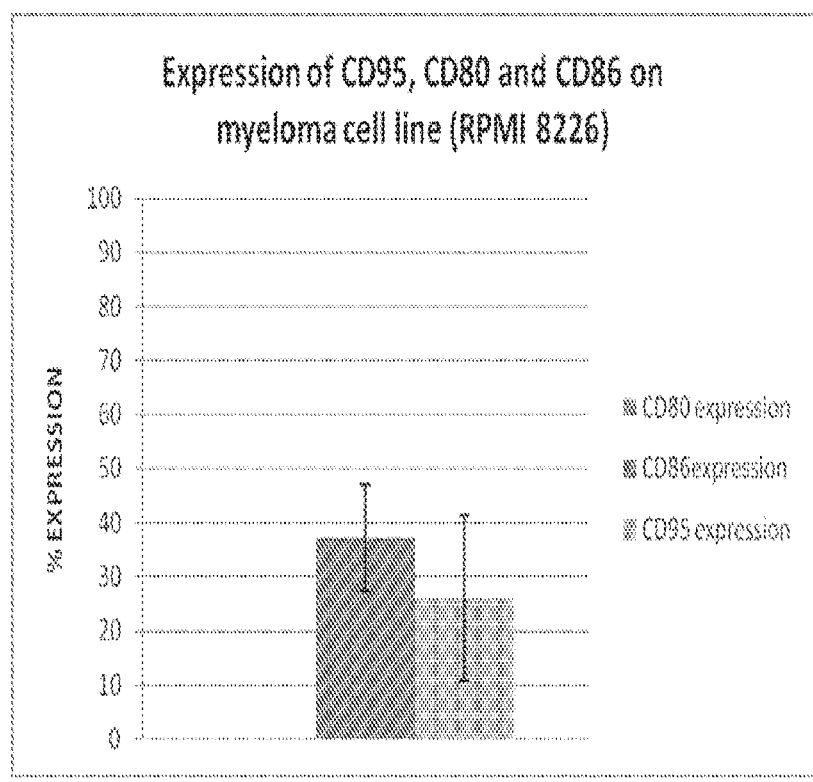
Figure 14:
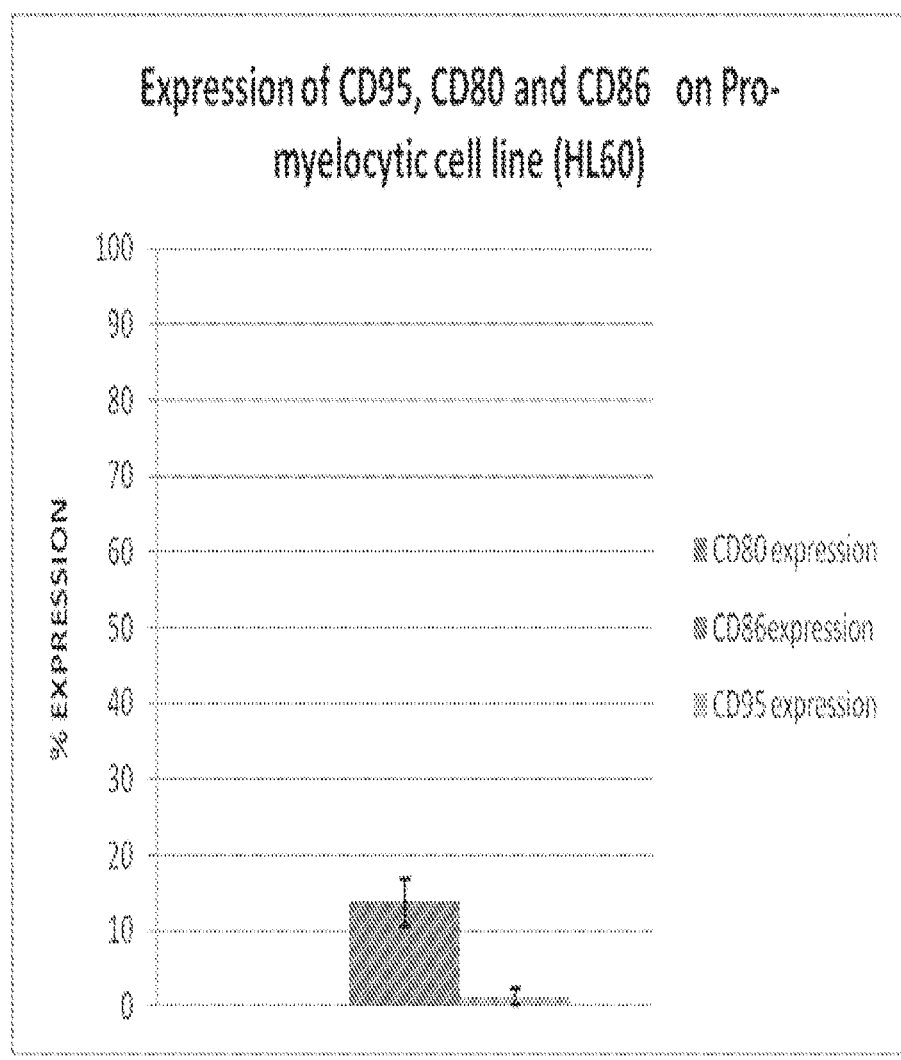

The human myeloma cell line, RPMI 8226, was then tested and as seen in FIG. 9 found that though their sensitivity to CTLA4-FasL is lower than that of the B cell lymphoma cell line, they do respond to higher concentrations of CTLA4-FasL. In contrast, promyelocytic leukemia cells were resistant to CTLA4-FasL's cytotoxic effect (FIG. 10).

The difference in susceptibility to CTLA4-FasL's action can be explained by the different expression of the surface molecules capable of binding the fusion protein. The expression of CD80 and CD86, which bind CTAL4, and the expression of CD95 (Fas receptor, which binds FasL) were then tested on the four cell lines. As can be seen in FIGS. 11-14, the two highly sensitive cell lines, namely Raji and JY, express all three surface molecules. The RPMI 8226, human multiple myeloma cell line, that exhibited intermediate sensitivity to CTLA4-FasL express both the Fas receptor and CD86, however in lower levels than the B cell lines, and do not express CD80 at all. The promyelocitic leukemia cells, that are not affected by CTLA4-FasL show low level of expression of CD86, and very low levels of Fas receptor.

Figure 15:
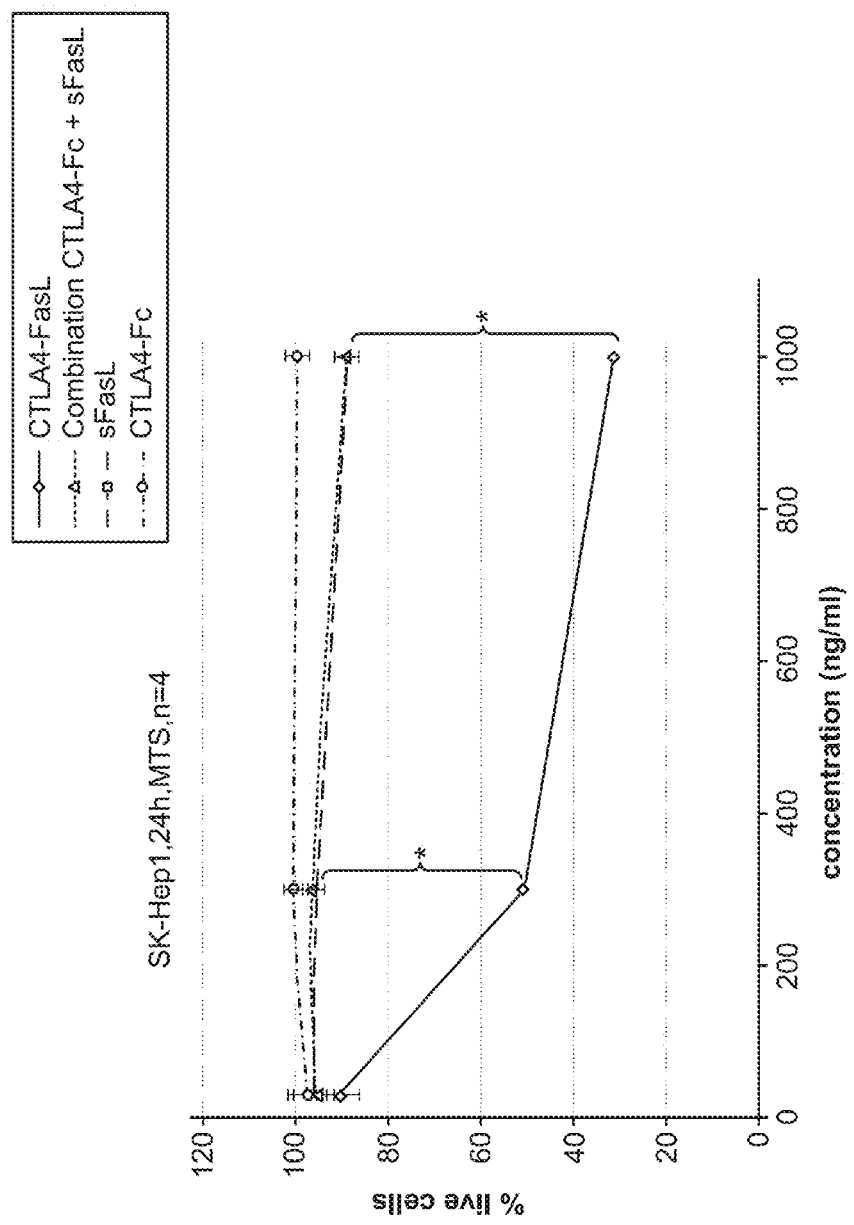
FIG. 15 shows that CTLA4-FasL exhibited a cytotoxic effect against SK-Hep1 hepatoma cells.
Figure 16:
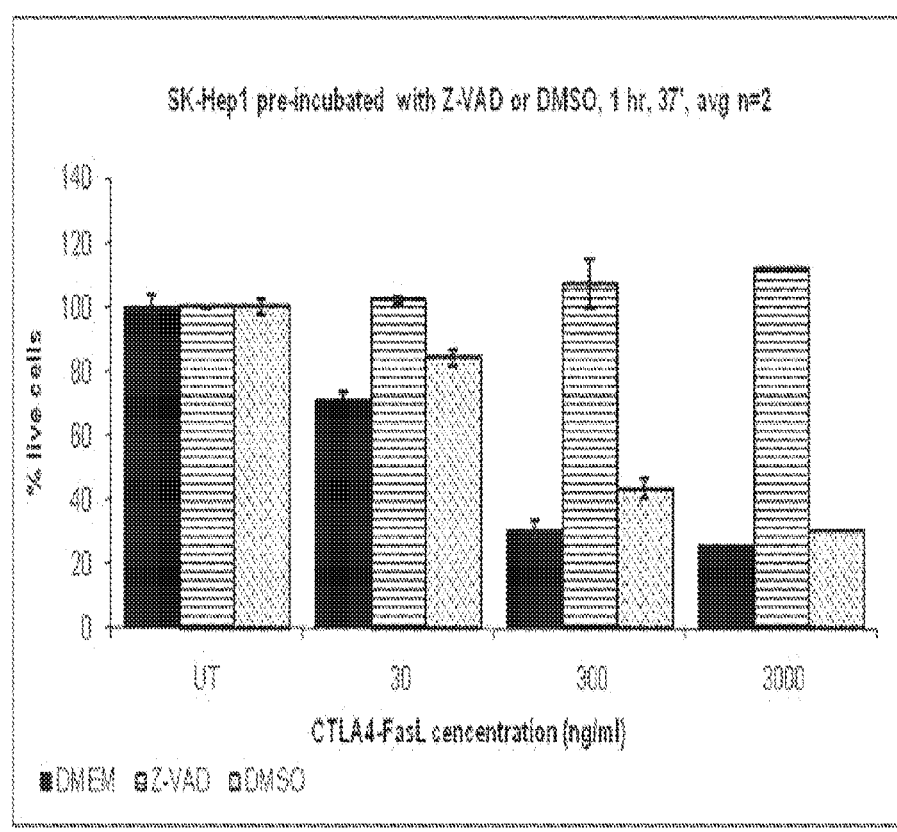
FIG. 16 shows that the pan-caspase inhibitor, zVAD, completely abolished CTLA4-FasL effect.

The analysis was extended to other cancer cell lines, namely, SK-Hep1 hepatoma cells. As can be seen in FIG. 15, CTLA4-FasL exhibited a cytotoxic effect against this tumor line, albeit with somewhat different kinetics; CTLA4-FasL was by far more potent than CTAL4-Fc, soluble FasL or the combination of the latter. Using this cell line, the effect of inhibition of apoptosis mediated by caspases on CTLA4-FasL's effect was tested. As shown in FIG. 16, the pan-caspase inhibitor, zVAD completely abolished CTLA4-FasL effect, indicating that its cytotoxic effect is apoptosis based.

Whereas particular embodiments of this invention have been described above for purposes of illustration, it will be evident to those skilled in the art that numerous variations of the details of the present invention may be made without departing from the invention as defined in the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A method of treating multiple myeloma, benign plasma cell disorder or premalignant forms of multiple myeloma in a subject, comprising administering to the subject a CD40-FasL chimeric protein, wherein cells of said multiple myeloma, said benign plasma cell disorder or said premalignant forms of multiple myeloma express CD40L.

2. The method of claim 1, wherein said multiple myeloma is selected from the group consisting of multiple myeloma cancers which produce light chains of kappa-type and/or light chains of lambda-type; aggressive multiple myeloma; smoldering multiple myeloma (SMM), indolent multiple myeloma, and primary amyloidosis.

3. The method of claim 2, wherein said aggressive multiple myeloma is primary plasma cell leukemia (PCL).

4. The method of claim 1, wherein said benign plasma cell disorder is selected from the group consisting of MGUS (monoclonal gammopathy of undetermined significance) and/or Waldenstrom's macroglobulinemia (WM, also known as lymphoplasmacytic lymphoma) which may proceed to multiple myeloma.

5. The method of claim 4, to halt the progression of the benign plasma cell disorder to a malignant form of multiple myeloma.

6. The method of claim 1, wherein said chimeric protein is administered as a pharmaceutical composition comprising said chimeric protein and a pharmaceutical carrier, adapted for treatment of said multiple myeloma, said benign plasma cell disorder or said premalignant forms of multiple myeloma.

7. The method of claim 6, wherein said multiple myeloma is selected from the group consisting of multiple myeloma cancers which produce light chains of kappa-type and/or light chains of lambda-type; aggressive multiple myeloma; smoldering multiple myeloma (SMM), indolent multiple myeloma, and primary amyloidosis.

8. The method of claim 7, wherein said multiple myeloma is primary plasma cell leukemia (PCL).

9. The method of claim 6, wherein said benign plasma cell disorder is selected from the group consisting of MGUS (monoclonal gammopathy of undetermined significance) and/or Waldenstrom's macroglobulinemia (WM, also known as lymphoplasmacytic lymphoma) which may proceed to multiple myeloma.

10. The method of claim 9, to halt the progression of the benign plasma cell disorder to a malignant form of multiple myeloma.

11. A method of treating multiple myeloma, benign plasma cell disorder or premalignant forms of multiple myeloma in a subject, comprising administering to the subject a CTLA4-FasL chimeric protein.

12. The method of claim 11, wherein cells of said multiple myeloma, said benign plasma cell disorder or said premalignant forms of multiple myeloma express B7.

13. The method of claim 11, wherein said multiple myeloma is selected from the group consisting of multiple myeloma cancers which produce light chains of kappa-type and/or light chains of lambda-type; aggressive multiple myeloma; smoldering multiple myeloma (SMM), indolent multiple myeloma, and primary amyloidosis.

14. The method of claim 13, wherein said aggressive multiple myeloma is primary plasma cell leukemia (PCL).

15. The method of claim 11, wherein said benign plasma cell disorder is selected from the group consisting of MGUS (monoclonal gammopathy of undetermined significance)

and/or Waldenstrom's macroglobulinemia (WM, also known as lymphoplasmacytic lymphoma) which may proceed to multiple myeloma.

16. The method of claim 15, to halt the progression of the benign plasma cell disorder to a malignant form of multiple myeloma.

17. The method of claim 11, wherein said chimeric protein is administered as a pharmaceutical composition comprising said chimeric protein and a pharmaceutical carrier, adapted for treatment of said multiple myeloma, said benign plasma cell disorder or said premalignant forms of multiple myeloma.

18. The method of claim 17, wherein cells of said multiple myeloma, said benign plasma cell disorder or said premalignant forms of multiple myeloma express B7.

19. The method of claim 17, wherein said multiple myeloma is selected from the group consisting of multiple myeloma cancers which produce light chains of kappa-type and/or light chains of lambda-type; aggressive multiple myeloma; smoldering multiple myeloma (SMM), indolent multiple myeloma, and primary amyloidosis.

20. The method of claim 19, wherein said multiple myeloma is primary plasma cell leukemia (PCL).

21. The method of claim 11, wherein said benign plasma cell disorder is selected from the group consisting of MGUS (monoclonal gammopathy of undetermined significance) and/or Waldenstrom's macroglobulinemia (WM, also known as lymphoplasmacytic lymphoma) which may proceed to multiple myeloma.

22. The method of claim 21, to halt the progression of the benign plasma cell disorder to a malignant form of multiple myeloma.

* * * * *